(12) United States Patent
Che

(10) Patent No.: US 9,023,490 B2
(45) Date of Patent: May 5, 2015

(54) EXTENDED PI-CONJUGATED PLATINUM (II) COMPLEXES

(75) Inventor: Chi Ming Che, Hong Kong (HK)

(73) Assignee: Versitech Limited, Pokfulam Road, Hong Kong (CN)

( * ) Notice: Subject to any disclaimer, the term of this patent is extended or adjusted under 35 U.S.C. 154(b) by 1430 days.

(21) Appl. No.: 12/137,742

(22) Filed: Jun. 12, 2008

(65) Prior Publication Data

US 2008/0309227 A1    Dec. 18, 2008

Related U.S. Application Data

(60) Provisional application No. 60/944,423, filed on Jun. 15, 2007.

(51) Int. Cl.
| | |
|---|---|
| *H01J 1/63* | (2006.01) |
| *C07F 15/00* | (2006.01) |
| *B05D 5/06* | (2006.01) |
| *C09K 11/06* | (2006.01) |
| *H01L 51/00* | (2006.01) |
| *H01L 51/50* | (2006.01) |

(52) U.S. Cl.
CPC .............. *C07F 15/0086* (2013.01); *C09K 11/06* (2013.01); *C09K 2211/1007* (2013.01); *C09K 2211/1011* (2013.01); *C09K 2211/1029* (2013.01); *C09K 2211/1044* (2013.01); *C09K 2211/1088* (2013.01); *C09K 2211/1092* (2013.01); *C09K 2211/185* (2013.01); *H01L 51/0081* (2013.01); *H01L 51/0087* (2013.01); *H01L 51/5016* (2013.01); *H01L 51/5036* (2013.01); *H01L 51/5096* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 3,172,862 A | 3/1965 | Gurnee et al. | |
| 4,356,429 A | 10/1982 | Tang | |
| 5,247,190 A | 9/1993 | Friend et al. | |
| 6,515,298 B2 | 2/2003 | Forrest et al. | |
| 7,026,480 B2 | 4/2006 | Che et al. | |
| 7,452,613 B2 * | 11/2008 | Poplavskyy et al. | 428/690 |
| 2002/0182441 A1 | 12/2002 | Lamansky et al. | |
| 2003/0205707 A1 | 11/2003 | Chi-Ming | |
| 2004/0018380 A1 * | 1/2004 | Aziz et al. | 428/690 |
| 2005/0233167 A1 * | 10/2005 | Che et al. | 428/690 |

(Continued)

FOREIGN PATENT DOCUMENTS

WO      9013148      11/1990

OTHER PUBLICATIONS

Kui et al. (Chem. Eur. J. 2007, 13, pp. 417-435).*
Baik et al. J. Organometallic Chem. 691 (2006) 5900-5910.*

(Continued)

*Primary Examiner* — J. L. Yang
(74) *Attorney, Agent, or Firm* — Eaton & Van Winkle LLP; Robert D. Katz, Esq.

(57) ABSTRACT

The invention provides organometallic complexes comprising an extended π-conjugated tridentate ligand having a platinum center in which chemical and/or physical properties of the complexes may be modified by changing the structure of the ligands. The complex finds use in devices incorporated into electroluminescent devices, flat panel displays, organic light emitting devices, polymer light emitting devices, transistors, serrors, and lasers.

26 Claims, 17 Drawing Sheets

(56) References Cited

U.S. PATENT DOCUMENTS

2006/0094875 A1* 5/2006 Itoh et al. ............................ 546/2
2006/0204787 A1* 9/2006 Sano et al. .................... 428/690

OTHER PUBLICATIONS

Lu et al. Chem. Commun. 3 (2002) 206-207.*
Kido et al., "Multilayer White Light-Emitting Organic Electroluminescent Device", *Science* 267:1332-1334 (1995).
Tung et al., "5.2: A High Efficiency Phosphorescent White OLED for LCD Backlight and Display Applications", *SID 04 Digest* 48-51 (2004).
B. W. D'Andrade et al., "Controlling Exciton Diffusion in Multilayer White Phosphorescent Organic Light Emitting Devices," *Adv. Mater.* 14: 147-151 (2002).
B. W. D'Andrade et al., "Efficient Organic Electrophosphorescent White-Light-Emitting Device with a Triple Doped Emissive Layer," *Adv. Mater.* 16: 624-628 (2004).
M. A. Baldo et al., "Highly Efficient Phosphorescent Emission from Organic Electroluminescent Devices," *Nature*, 395: 151 (1998).
F. F. Blicke et al., "The Preparation of β-Keto Amines by the Mannich Reaction" *J. Am. Chem. Soc.* 64, 451 (1942).
G. W. V. Cave et al., "Efficient Synthesis of Pyridines via a Sequential Solventless Aldol Condensation and Michael Addition", *J. Chem. Soc., Perkin Trans. 1*, 3258-3264 (2001).
C.M. Che et al., "Tetradentate Schiff Base Platinum (II) Complexes as New Class of Phosphorescent Materials for High-Efficiency and White-light Electroluminescent Devices," Chem. Comm., 1484-1485 (2004).
K. O. Cheon et al., "Bright White Small Molecular Organic Light-emitting Devices Based on a Red-Emitting Guest-Host Layer and Blue-emitting 4,4'-bis (2,2'-diphenylvinyl)-1,1'-biphenyl," *Appl. Phys. Lett.* 81: 1738 (2002).
K.Y. Ho et al., "A Blue Photoluminescent $[Zn(L)(CN)_2]$ (L=2,2'-dipyridylamine) Material with a Supramolecular One-dimensional Chain Structure," *Chem. Commun.*, 2101 (1998).
P. S. Kendurkar et al., "Synthesis of Some New 2,4,6-Triaryl-Substituted Pyridines via Aroylmethylenepyridinium Ylides," *J. Chem. Eng. Data*, 19: 184 (1974).
L. C. King et al., "The Reaction of Ketones with Iodine and Pyridine," *J. Am. Chem. Soc.* 70, 239 (1948).
S.C.F. Kui et al. "Structures, Photoluminescence, and Reversible Vapoluminescence Properties of Neutral Platinum (II) Complexes Containing Extended π-Conjugated Cyclometalated Ligands", *J. Am. Chem. Soc.* 128, 25: 8297 (2006).
C. W. Ko et al., "Bright White Organic Light-emitting Diode," *Appl. Phys. Lett.* 79: 4234 (2001).
C.C. Kwok et al. "Self-Aggregated Phosphorescent Platinum (II) Polymeric Material from Modified Poly (4-vinylpyridine)", *Chem. Commun.* 2512-2513 (2004).
C.C. Kwok et al. "[(ONN)PtX] Complexes as a New Class of Light-Emitting Materials for Electrophosphorescent Devices," *Inorg. Chem.* 44:4442-4444 (2005).

Y.Y. Lin et al., "Structural, Photophysical, and Electrophosphorescent Properties of Platinum (II) Complexes Supported by Tetradentate $N_2$ $O_2$ Chelates," *Chem. Eur. J.* 9:1263-1272.
X.Q. Lin et al. "A Novel Yellow Florescent Dopant for High-Performance Organic Electroluminescent Devices," *Chem. Mater.* 13:456-458 (2001).
S. Lamansky, et al. "Highly Phosphorescent Bis-Cyclometalated Iridium Complexes: Synthesis, Photophysical Characterization, and Use in Organic Light Emitting Diodes," *J. Am. Chem. Soc.* 4304-4312 (2001).
J. Y. Legros et al. "Syntheses of Acetylquinolines and Acetylisoquinolines Via Palladium-Catalyzed Coupling Reactions," *Tetrahedron* 57:2507-2514 (2001).
W. Lu et al. "Light-Emitting Tridentate Cyclometalated Platinum (II) Complexes Containing σ-Alkynyl Auxiliaries: Tuning of Photo- and Electrophosphorescence," J. Am. Chem. Soc. 126:4958-4971 (2004).
W. Lu et al. "[(CNN) Pt(C=C$n$R] (HCNN=6-aryl-2,2'-bipyridine, $n$=1-4, R=aryl, $SiME_3$) as a New class of Light-Emitting Materials and Their Applications in Electrophosphorescent Devices," *Chem. Commun.* 206-207 (2002).
Y. Ma et al. "Electroluminescence from Triplet Metal-ligand Charge-Transfer Excited State of Transition Metal Complexes," *Synthetic Metals* 94:245-248, (1998).
Y. Ma et al. "Light-Emitting Diode Device from a Luminescent Organocopper (I) Compound," *New J. Chem.* 263-265 (1999).
Y. Ma et al. "A Blue Electroluminescent Molecular Device from a Tetranucleaur Zinc (II) Compound $[Zn_4O(AID)_6$ (AID=7-azaindolate)," *Chem. Comm.* 2491-2492 (1998).
Y. Ma et al. "Triplet Luminescent Dinuclear-Gold (*I*) Complex-Based Light-Emitting Didoes with Low Turn-On Voltage," *Appl. Phys. Lett.* 1361-1363 (1999).
M. Mazzeo et al. "Bright Oligothiophene-Based Light Emitting Diodes," *Synthetic Metals* 139:671-673 (2003).
F. Neve and A. Crispini "Anisometric Cyclometalated Palladium (II) and Platinum (II) Complexes. Structural and Photophysical Studies," *Inorg. Chem.* 36:6150-6156 (1997).
R.G. Pearson "Mechanism of the Acetophenone-Iodine-Pyridine Reaction," *J. Am. Chem. Soc.* 69, 3100 (1947).
C.W. Tang and S.A. VanSlyke "Organic Electroluminescent Diodes," *Appl. Phys. Lett. 51,* 12: 913-915 (1987).
S. Tokito et al. High-Efficiency White Phosphorescent Organic Light-Emitting Devices with Greenish-Blue and Red-Emitting Layers, *Appl. Phys. Lett.* 2459-2461 (2003).
Y. Sun et al. "Management of Singlet and Triplet Excitons for Efficient White Organic Light-Emitting Devices," *Nature* 440:908-912 (2006).
H.F. Xiang et al. "High-Efficiency Red Electrophosphorescence Based on Neutral bis (pyrrole)-diimine Platinum (II) Complex," Chem. Comm. 1408-1410 (2005).
S.C. Yu et al. "Self-Assembled Electroluminescent Polymers Derived from Terpyridine-Based Moieties," Adv. Matter. 1643-1647, (2003).

\* cited by examiner

EXTENDED PI-CONJUGATED PLATINUM (II) COMPLEXES

CROSS REFERENCE TO RELATED APPLICATION

This application claims the benefit of U.S. Provisional Application No. 60/944,423, filed Jun. 15, 2007, the entire contents of which are hereby incorporated by reference.

Throughout this application, various publications are referenced by full citations. The disclosures of these publications in their entireties are hereby incorporated by reference into this application.

BACKGROUND

Organic Light-Emitting Devices (OLEDs) typically encompass display devices that sandwich carbon-based films between two charged electrodes, one a metallic cathode and one a transparent anode, often glass. The films include a hole-injection layer, a hole-transport layer (HTL), an emissive layer (EL) and an electron-transport layer (ETL). If voltage is applied to the OLED cell, injected positive (holes) and negative (electron) charges may recombine in the emissive layer and create electroluminescent light.

Organic electroluminescence was first observed and studied in the 1960's U.S. Pat. No. 3,172,862 (Gurnee). In the 1980's, a double-layer structure for an OLED was disclosed by Tang (U.S. Pat. No. 4,356,429 (Tang); C. W. Tang et al., *Appl. Phys. Lett.* 51, 12: 913 (1987)). The discovery was based at least in part on employing a multilayer structure including an emitting layer and a hole transport layer of a suitable organic substrate. $Alq_3$ (q=deprotonated 8-hydroxyquinolinyl) was chosen as the emitting material and was shown to provide relative advantages. For example, it may form relatively uniform thin films under 1000 Å using vacuum deposition. It is also a good charge carrier and it exhibits strong fluorescence. A conducting polymer-based OLED or PLED (polymer light-emitting device) was disclosed shortly after that by Friend at Cambridge University (Friend, WO Patent 90/13148 (Friend); U.S. Pat. No. 5,247,190 (Friend)).

Since then, research on OLEDs and materials used in these devices has continued. OLED technology may be gaining marketplace acceptance, as suggested in a commercial report by Stanford Resources (http://www.stanfordresources.com), for example. OLEDs provide several advantages including: (1) low operating voltage; (2) thin, monolithic structure; (3) emitting light, rather than modulating light; (4) good luminous efficiency; (5) full color potential; and (6) high contrast and resolution. These advantages suggest possible use of OLEDs in flat panel displays.

One aspect related to the operation of an OLED is an organic luminophore or organometallic luminophore. An exciton, which includes a bound, excited electron and hole pair, may be generated inside an emitting layer (EL). If the exciton's electron and hole combine, a photon (visible light) may be emitted. To create excitons, an emitting layer (EL) may be sandwiched between electrodes of differing work functions. Electrons may be injected into one side from a metal cathode (e.g., Aluminium (Al), calcium (Ca), Magnesium-Silver alloy (Mg—Ag) are common cathode materials) via a electron transporting layer (ETL), while holes may be injected in the other side from an anode (e.g., Indium tin oxide (ITO) is a common transparent anode) via a hole transporting layer (HTL). The electron and hole may move into the emitting layer (EL) and may meet to form an exciton. An electroluminescent material in the emitting layer (EL) may be present in a separate emitting layer between the ETL and the HTL in what is referred as a multi-layer heterostructure. One possible embodiment of a basic heterostructure of an OLED is shown by a schematic diagram in FIG. 1, for example.

A major challenge in OLED manufacture is tuning a device such that a balancing number of holes and electrons meet in the emitting layer. This is difficult because, in an organic compound, the mobility of an electron is lower than that of a hole. In general, an exciton may be in one of two states, a singlet state (25%) or a triplet state (75%). Materials employed in an emissive layer are typically organic fluorophors, which emit light if a singlet exciton forms. However, by incorporating transition metals into a small-molecule OLED, the triplet and singlet states may be mixed by spin-orbit coupling, which may lead to emission from the triplet state. Triplet (phosphorescent) emitters can be four times more efficient than singlet emitters (S. R. Forrest et al., *Nature* 395: 151 (1998); H. ersin, *Top. Curr. Chem.* 241: 1 (2004)). In some cases, buffer layers and/or other functional layers may also be incorporated to improve the performance of the device. Likewise, OLEDs in which the electroluminescent emitters are the same materials that function either as an ETL or a HTL may be referred to here as single-layer heterostructures.

In addition to emissive materials that are present as the predominant component located between a hole transporting layer (HTL) and an electron transporting layer (ETL), another efficient luminescent material may be present in relatively low concentrations as a dopant in these layers to realize color tuning and efficiency improvement. If a dopant is present, the predominant material in the charge carrier layer may be referred to as a host. Materials as hosts and dopant may be matched so as to have a relatively high level of energy transfer from the host to the dopant, and to yield emission with a relatively narrow band centered near a selected spectral region with relatively high-efficiency and relatively high-brightness. The quantum efficiency of an electrofluorescence device is typically limited by the low theoretical ratio of singlet exciton (25%) compared to triplet exciton (75%) upon electron-hole recombination from electrical excitation. In contrast, if phosphorescent emitters are employed, the potentially for relatively high energy/electron transfer from a host to a phosphorescent emitters may result in improved electroluminescent efficiency (S. R. Forrest et al., *Nature* 395: 151 (1998); Y. G. Ma et al., *Synth. Met.* 94: 245 (1998)). Several phosphorescent OLED systems have been fabricated and have been demonstrated to be of relatively high-efficiency and relatively high-brightness.

OLEDs may be fabricated using materials that provide electrophosphorescent emission corresponding to one of the three primary colors, that is, red (R), green (G) and blue (B) so that they may be used as a component layer in full-color display devices, for example. Such materials may also be capable of being deposited as thin films using vacuum deposition techniques, which is a common method for OLED fabrication, so that the thickness of the emitting layer may be precisely controlled.

Improved methods of fabricating OLEDs and methods of making luminescent materials that may be employed in OLEDs continue to be sought.

SUMMARY OF THE INVENTION

An organometallic complex comprising:
an extended π-conjugated tridentate ligand having a platinum center, wherein the ligand comprises an extended π-conjugated tridentate ligand having one of the following structures:

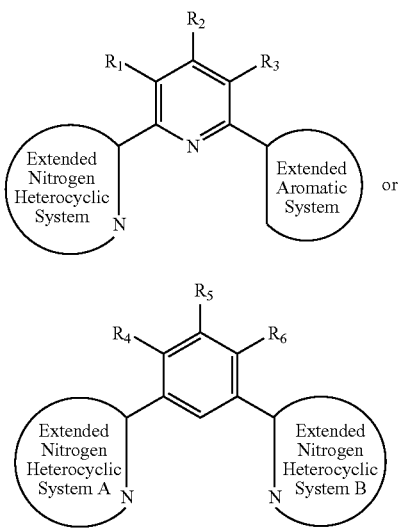

wherein $R_1$-$R_6$ are independently hydrogen halogen hydroxyl an unsubstituted alkyl, a substituted alkyl, cycloalkyl, aryl, acyl, alkoxy, acyloxy, amino, acylamino, aralkyl, cyano, carboxyl, thio, styryl, aminocarbonyl, carbamoyl, aryloxycarbonyl, phenoxycarbonyl, or an alkoxycarbonyl;

wherein the R1-R6 substituents form a ring together with the group on which they are substituted; and wherein the extended nitrogen heterocyclic aromatic systems and the extended aromatic systems comprise fused ring systems including at least two aromatic and/or heterocyclic aromatic rings fused together.

BRIEF DESCRIPTION OF THE DRAWINGS

Other objects, features, and advantages of the invention may be understood by reference to the following detailed description of the preferred embodiment, taken together with the accompanying drawings, in which.

DETAILED DESCRIPTION OF THE PREFERRED EMBODIMENTS

Figure 1:
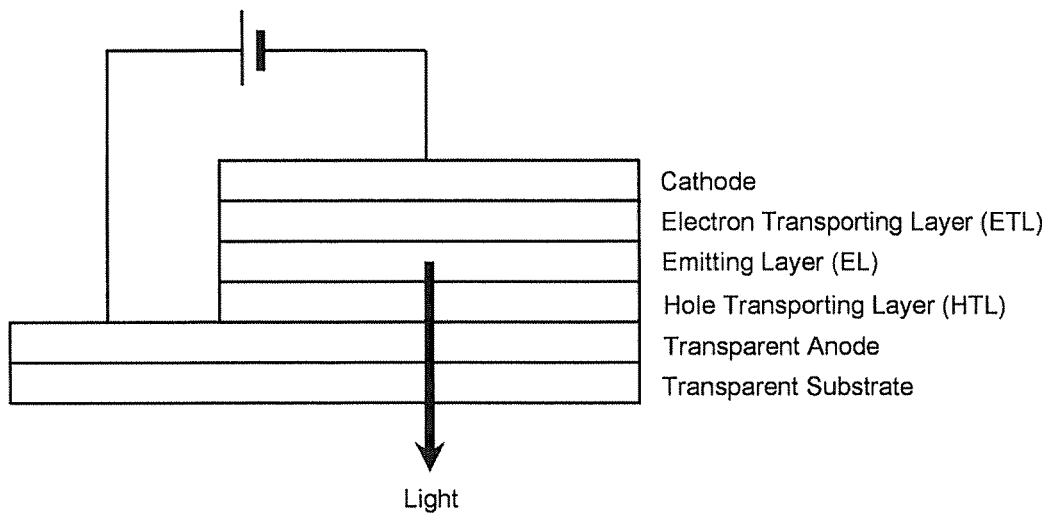
FIG. 1 is a schematic diagram of an embodiment of a basic hetero-structure OLED.

Recently, electro-phosphorescent materials with different color emissions have been disclosed. Thompson at al. at the University of Southern California and Forrest et al. at Princeton University jointly reported a family of iridium complexes exhibiting improved brightness and efficiencies (S. R. Forrest et al., U.S. Pat. No. 6,515,298 (2001); U.S. Pat. Appl. Publ. No. 20020182441 (2002) and *J. Am. Chem. Soc.*, 123: 4304 (2001). Another class of phosphorescent materials includes compounds having interactions between metal atoms having $d^{10}$ electron configuration, such as $Au_2$ (□-dppm) $Cl_2$, (dppm=bis(diphenylphosphino)methane) ($Y^2$. Ma et al., *Appl. Phys. Lett.* 74: 1361 (1998)). Recently, Che has demonstrated the use of metal organic complexes, such as (1) platinum (II) (*Inorg. Chem.*, 44, 13: 4442 (2005); *Chem. Commun.*, 1408 (2005); *Chem. Commun.*, 2512 (2004); *Chem. Commun.*, 1484 (2004); *J. Am. Chem. Soc.* 126, 15: 4958 (2004); *Chem. Eur. J.*, 9: 1263 (2003) and Chem. Commun., 206 (2002)), (2) copper(I) (*New J. Chem.*, 263 (1999)), (3) gold(I) (*Appl. Phys. Lett.*, 74: 1361 (1999)), and (4) zinc(II) complexes (*Chem. Commun.*, 2758 (2004); *Adv. Mater.*, 15:1643 (2003); *Chem. Commun.*, 2101 (1998) and *Chem. Commun.*, 2491 (1998)), as OLED materials. For example, Che demonstrated that cyclometallated Pt(II) complexes may be desirable for OLED applications at least in part due to their relative stability and brightness. For example, emission of light may be changed by varying the structure of the nitrogen heterocycle ligands to achieve yellow and red electroluminescence (C. M. Che et al., U.S. Pat. No. 7,026, 480 B2 (2006); U.S. Pat. Appl. Publ. No. 2005244672 (2005); U.S. Pat. Appl. Publ. No 2005233167 (2005); U.S. Pat. Appl. Publ. No. 20030205707 and references cited therein).

Although various phosphorescent metal complexes (such as, for example, Ir, Pt, Au, Cu and Zn, etc.), have been described as useful in an EL device, extended π-conjugated metal-based organometallic complexes have not been examined extensively. Recently, Che reported unique photo-luminescent properties of a series of neutral Platinum(II) complexes that included extended π-conjugated cyclometalated ligands (*J. Am. Chem. Soc.* 128, 25: 8297 (2006)). This result implied that extended π-conjugated cyclometalated ligand systems may provide organometallic Pt(II) complexes for use in phosphorescent materials that will exhibit useful light emissions.

White organic light-emitting devices (WOLEDs) are of interest at least in part because they may be used for full-color flat-panel displays with color filters, and as an alternative lighting source (C. W. Ko et al., *Appl. Phys. Lett.* 79: 4234 (2001); J. Kido et al., *Science*, 267: 1332 (1995); K. O. Cheon et al., *Appl. Phys. Lett.* 81: 1738 (2002)). Among the reported WOLEDs, electro-phosphorescent WOLEDs may be attractive at least in part due to their relatively high quantum and relative power efficiency. In comparison with their fluorescent counterparts that harvest singlet excitons, phosphorescent OLEDs are able to harness both singlet and triplet excitons generated by electrical injection, corresponding to a four-fold increase in efficiency compared to that achievable in singlet-harvesting fluorescent OLEDs (M. A. Baldo et al., *Nature*, 395: 151 (1998)). An electro-phosphorescent WOLED was first demonstrated by Thompson and Forrest et al., and it was a multiple layer architecture with three separate emission regions (B. W. D'Andrade et al., *Adv. Mater.* 14: 147 (2002)). Three phosphorescent materials, bis(4,6-di-fluorophenyl)-pyridinato-N,$C^2$) iridium (picolinate) [FIr(pic)], bis(2-(2'-benzo[4,5-a]thienyl)pyridinato-N,$C^3$) iridium (acetylacetonate) [Btp$_2$Ir(acac)] and bis(2-phenylbenzothiozolato-N,$C^{2'}$) iridium(acetylacetonate) [Bt$_2$Ir(acac)] were used as blue, red and yellow light sources, respectively, doped into a 4,4'-N,N'-dicarbazole-biphenyl (CBP) host. The device made from these materials exhibited a maximum external quantum efficiency of 5.2%. Following this work, Tokito et al. reported a high efficiency electro-phosphorescent WOLED with two separate emission regions (S. Tokito et al., *Appl. Phys. Lett.* 83: 2459 (2003)). Bis(2-(3,5-bistrifluoromethyl-phenyl)-pyridinato-N,$C^2$) iridium (picolinate) [(CF$_3$ppy)$_2$Ir (pic)] was used as a greenish-blue source, and [Btp$_2$Ir(acac)] as a red source to achieve a balanced white light emission. By adjusting doping concentration and thickness of the emissive layers, white light emission with maximum external quantum efficiency of 12% was achieved at a relatively low current density. To further improve efficiency and simplify device structure, Thompson and Forrest et al. employed a triple doped emissive layer to achieve efficient white light emissions (B. W. D'Andrade et al., *Adv. Mater.* 16: 624 (2004)). Still, blue, red and yellow dopants ([Fir(pic)], [Btp$_2$Ir(acac)] and [Bt$_2$Ir(acac)], respectively) were co-doped into a wide energy gap p-bis(triphenylsilyl)benzene (UGH2) host. By reducing the thickness of the emissive layer and confining charge and excitons, this device demonstrated a maximum external quantum efficiency of 12%, and a maximum power efficiency of 26 lm W$^{-1}$. Although phosphorescent WOLEDs have shown good performance, experiments have shown that blue electro-phosphorescent devices may exhibit short operational lifetimes that may limit color stability of an all-phosphor-doped WOLED (Y. J. Tung et al., *Proc. Soc. Inform. Display*, 35: 48 (2004)). Furthermore, using multiple emissive dopants may lead to differential aging of the various chromophores. An undesired shift in color coordinates as the device ages may result. In addition, in comparison with their fluorescent counterparts, WOLEDs employing phosphorescent blue dopants excited via a conductive host may introduce an approximately 0.8 eV exchange energy loss in power efficiency. To overcome these shortcomings, more recently, Forrest's group proposed a WOLED architecture based at least in part on phosphorescent/fluorescent material (Y. Sun et al., *Nature*, 440: 908 (2006)). A fluorescent emitting dopant was suggested to harness electrically generated high energy singlet excitons for blue emission, and phosphorescent dopants were suggested to harvest low-energy triplet excitons for green and red emission. A relatively high external quantum efficiency of 11% was obtained.

Embodiments of extended π-conjugation platinum(II) complexes and their derivatives are disclosed that may be employed to produce light-emitting materials. Likewise, such light-emitting materials may be employed in a variety of devices, including, OLEDs, for example, although claimed subject matter is not limited in scope in these previously mentioned two respects, of course. In one particular example, for example, extended π-conjugation platinum(II) complexes and their derivates may have their chemical and/or physical properties (including their photophysical properties) modified by employing ligands in a manner described in more detail below. For example, [(R—CNN)PtCl] type complexes may be employed as light-emitting materials. Such complexes are discrete organometallic molecules in nature, may be deposited as a thin layer by vacuum deposition, and may operate as emitters and/or materials for a variety of devices. Such devices may include, without limitation, electroluminescent (EL) devices (including organic light-emitting devices (OLEDs), white organic light-emitting devices (WOLEDs)), photovoltaic cells, field-effect transistors, sensors, lasers as well as non-linear optical materials (NLO), and/or the like. For example, organometallic light-emitting materials disclosed herein, such as extended π-conjugation platinum(II) complexes and their derivates, may be incorporated in flat panel displays, full-color flat-panel displays with color filters, lighting sources, and/or a variety of other devices.

As another example, organometallic light-emitting materials are disclosed which may be used as emitters or dopants in OLEDs and WOLEDs. More specifically, but without limitation, the design, synthesis, properties and applications of a family of emitters is disclosed which, if added in effective amounts to a suitable host material, including emissive compounds, electron transporting compounds and hole transporting compounds, may tune color emissions within the visible color range and may enhance device efficiency and brightness. Additionally or alternatively, the thermal stability of these emitters may be sufficient to allow sublimation, so that they may be readily incorporated into devices using vacuum deposition techniques. Therefore, as an example, EL devices prepared from vacuum-deposited materials may be realized.

The emitters described herein may comprise, without limitation, platinum(II) complexes with chemical structures of Structure I and/or Structure II as follows:

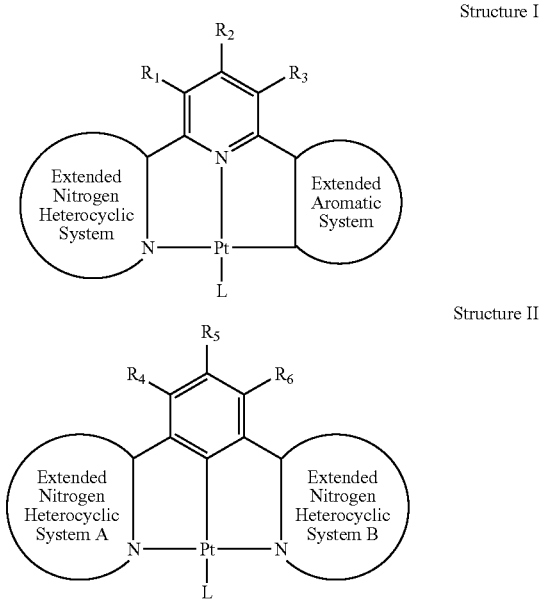

Structure I

Structure II

For this particular example embodiment, $R_1$-$R_6$ comprise substituents independently selected from the group of substituents consisting essentially of hydrogen; halogen; hydroxyl; unsubstituted or substituted alkyl group, cycloalkyl group, aryl group, acyl group, alkoxy group, acyloxy group, amino group, acylamino group, aralkyl group, cyano group, carboxyl group, thio group, styryl group, aminocarbonyl group, carbamoyl group, aryloxycarbonyl group, phenoxycarbonyl group, and alkoxycarbonyl group. Likewise, for this embodiment, the substituents together with the group on which they are substituted may form a ring with the substituents being the listed above hydrogen, halogens and hydroxyl groups, as well as recognized donor and acceptor groups. Extended nitrogen heterocyclic aromatic systems and extended aromatic systems may comprise fused ring systems including at least two aromatic and/or heterocyclic aromatic rings fused together. Further, L here may represent a ligand atom or molecule bearing a negative charge. In the L-M metal bond, where M represents the metal atom of the organometallic complex, more of the electron density is localized on L, the ligand; the L-M bond may be ionic or covalent in character. For example, L may represent a halogen atom that is fluoride, chloride, bromide, or iodide. L may also be chosen so that it forms a carbon metal bond in the organometallic complex; for example, L may represent a cyanide group, an aryl group, an substituted aryl group, a cyclopentenyl group, a vinyl group, an allyl group, an alkyl group, an acetylide group (e.g., containing alkyl, aryl, substituted aryl, and tri(alkyl)silky on the acetylide group). L may also represent R'E, where E forms a bond to the metal (Pt or Pd) and where E represents N, O, S, or Se and R' represents a substituent (e.g., an aryl group or an alkyl group or a carbonyl group or sulfonyl group).

As summarized above, organometallic complexes may comprise, for example, platinum. In one particular example, the oxidation state of platinum metal may comprise +2. In such a situation, the metal may form a complex with an extended π-conjugation tridentate ligand. An extended π-conjugation tridentate ligand in this context may, for example, comprise a ligand molecule that coordinates to the metal through two nitrogen donor bonds and a carbon bond. The tridentate ligand may therefore bear a formal negative charge localized at the site of a metal-carbon bond. As a multidentate-ligand forms a ring system with a central metal atom in a platinum(II) complex, for example, the ligand may be said to be cyclometallated. Examples of suitable π-conjugation tridentate ligands, without limitation, may be represented by Ligand I and Ligand II, as follows:

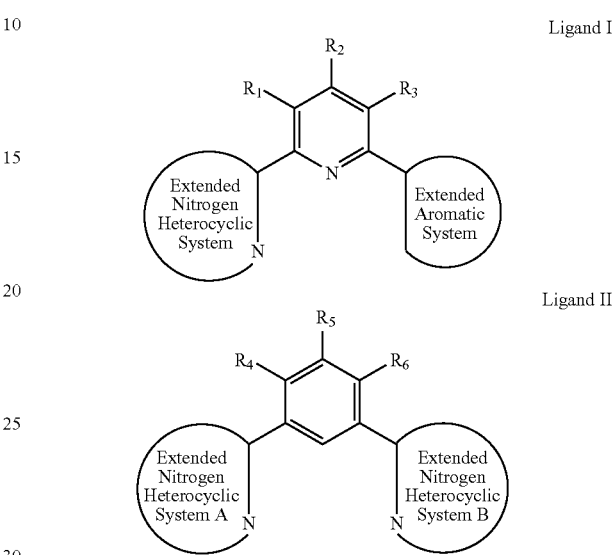

Ligand I

Ligand II

In this example embodiment, $R_1$-$R_6$ may comprise substituents independently selected from the group of substitutents consisting essentially of hydrogen; halogen; hydroxyl; unsubstituted or substituted alkyl group, cycloalkyl group, aryl group, acyl group, alkoxy group, acyloxy group, amino group, acylamino group, aralkyl group, cyano group, carboxyl group, thio group, styryl group, aminocarbonyl group, carbamoyl group, aryloxycarbonyl group, phenoxycarbonyl group, and alkoxycarbonyl group. In this particular embodiment, the substituents together with the group on which they are substituted may form a ring with the substituents being the listed above hydrogen, halogens and hydroxyl groups, as well as recognized donor and acceptor groups.

Furthermore, an extended nitrogen heterocyclic system may comprise fused ring systems including at least two nitrogen heterocyclic aromatic rings fused together. Examples include, but are not limited to the following:

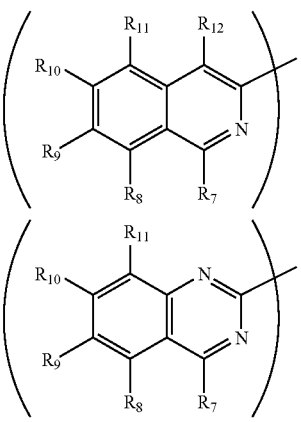

-continued

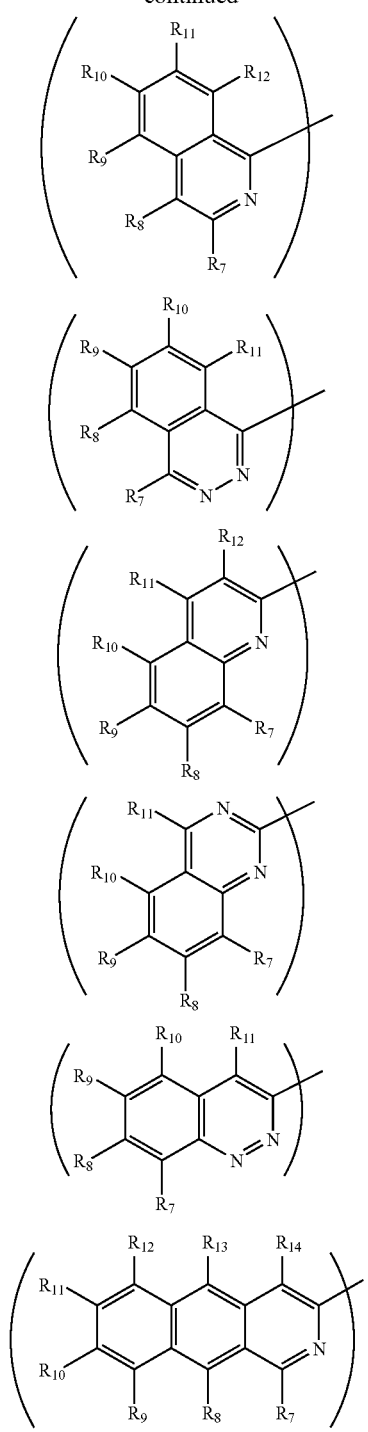

In this exemplary embodiment, $R_7$-$R_{14}$ may comprise substitutents independently selected from the group of substituents consisting essentially of hydrogen; halogen; hydroxyl; unsubstituted or substituted alkyl group, cycloalkyl group, aryl group, acyl group, alkoxy group, acyloxy group, amino group, acylamino group, aralkyl group, cyano group, carboxyl group, thio group, styryl group, aminocarbonyl group, carbamoyl group, aryloxycarbonyl group, phenoxycarbonyl group, and alkoxycarbonyl group. The substituents together with the group on which they are substituted may form a ring with the substituents being the listed above hydrogen, halogens and hydroxyl groups, as well as recognized donor and acceptor groups.

Furthermore, for this exemplary embodiment, an extended aromatic system may comprise fuse ring systems including at least 2 aromatic and/or heterocyclic aromatic rings fused together. Examples may include, but are not limited to the following:

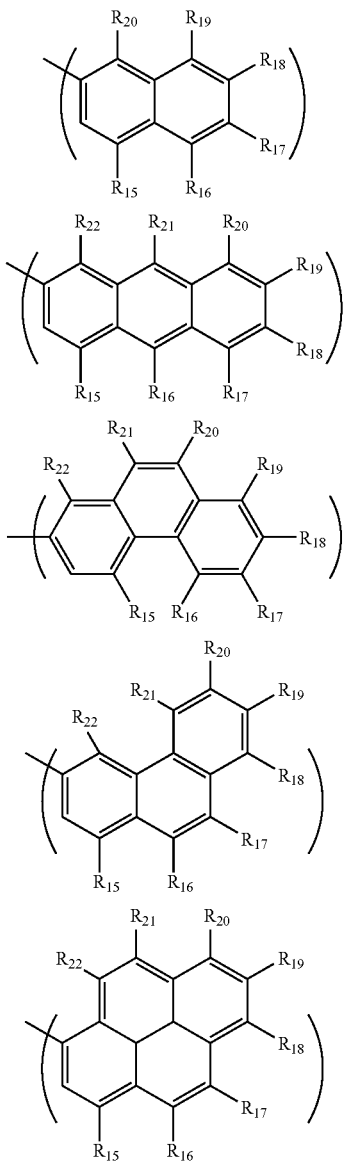

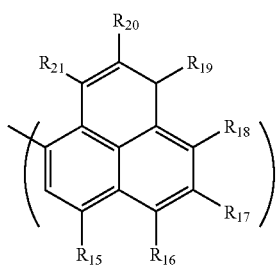

-continued

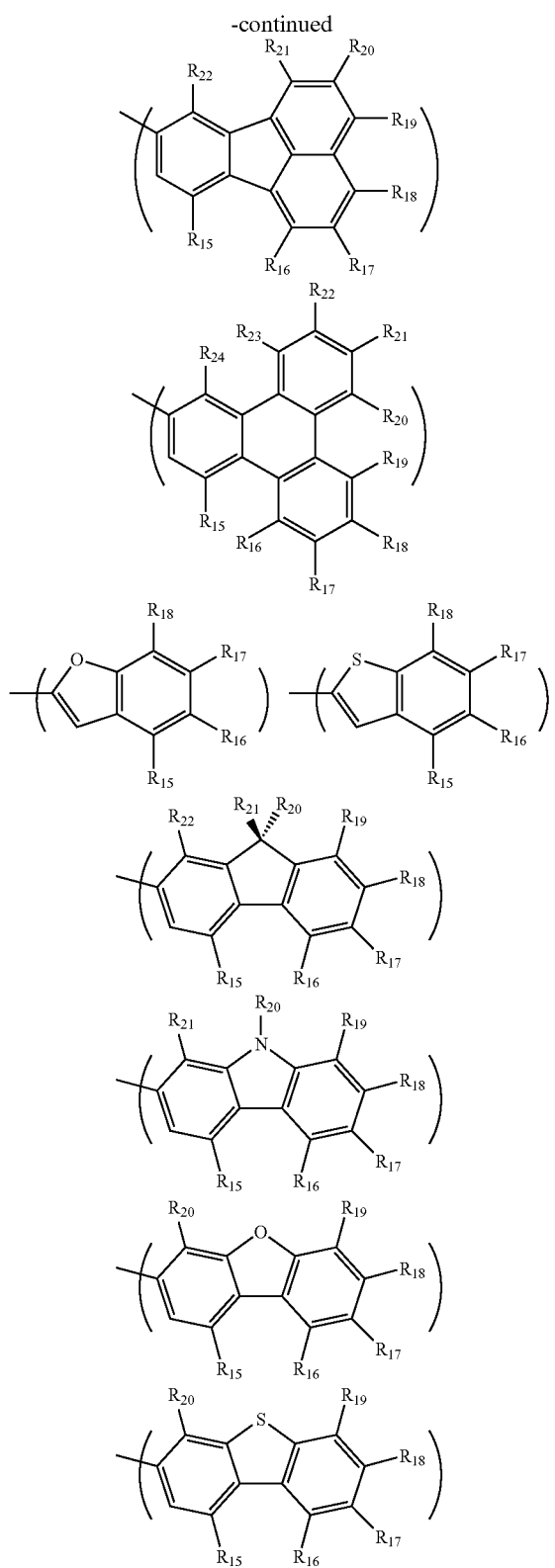

For this exemplary embodiment, $R_{15}$-$R_{22}$ may comprise substituents independently selected from the group of substitutents consisting essentially of hydrogen; halogen; hydroxyl; unsubstituted or substituted alkyl group, cycloalkyl group, aryl group, acyl group, alkoxy group, acyloxy group, amino group, acylamino group, aralkyl group, cyano group, carboxyl group, thio group, styryl group, aminocarbonyl group, carbamoyl group, aryloxycarbonyl group, phenoxycarbonyl group, and alkoxycarbonyl group. Likewise, for this exemplary embodiment, the substituents together with the group on which they are substituted may form a ring with the substituents being the listed above hydrogen, halogens and hydroxyl groups, as well as recognized donor and acceptor groups.

Representative examples of the ligands based at least in part on Ligand I are shown below.

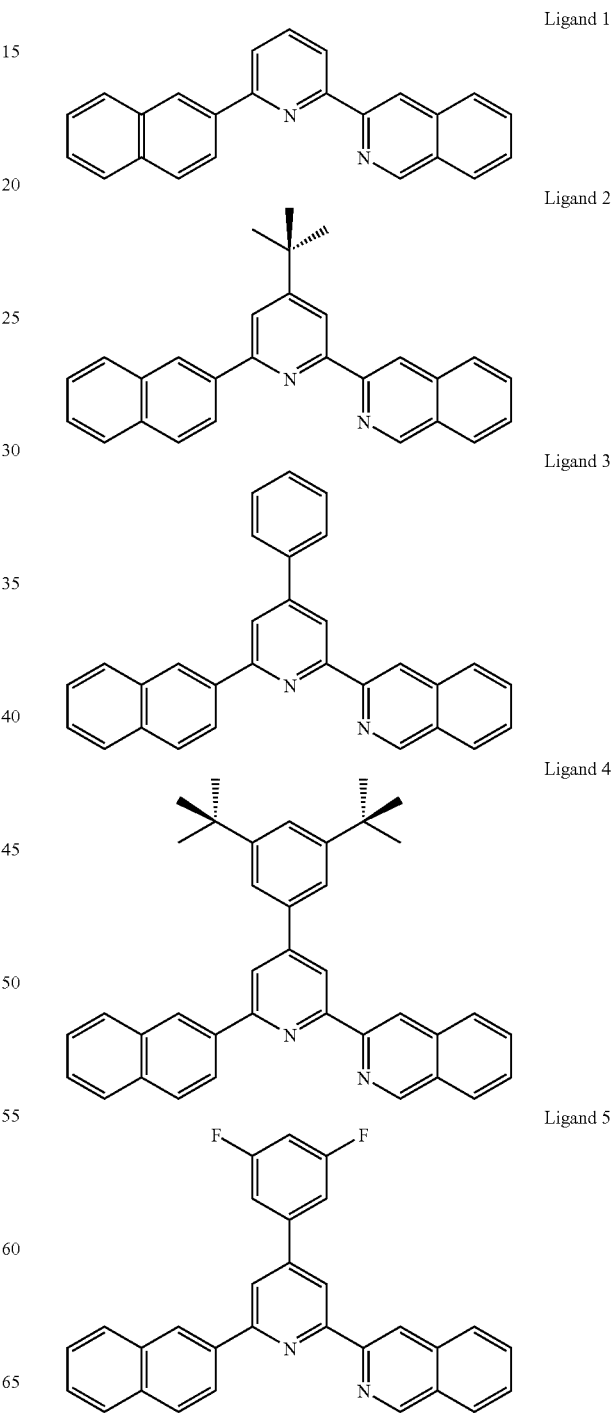

Ligand 6

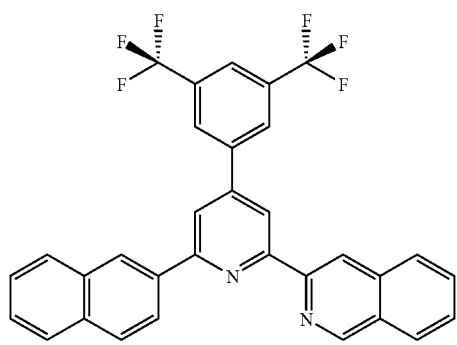

Furthermore, one embodiment of a method for effectively preparing the ligands in the representative examples is described below. Preparation of these ligands, however, is not limited to these examples.

For example, ligands 1-8 may be prepared based at least in part on a modification of the procedure described in P. S. Kendurkar et al., *J. Chem. Eng. Data,* 19: 184 (1974). Here, a mixture of 1-(2-oxo-2-(3'-isoquinolinyl)ethyl)pyridinium iodide, 3-dimethylamino-1-(2'-naphthyl)-propanone hydrochloride salt (for Ligand 1) or the corresponding α,β unsaturated ketone (for Ligands 2-8) and excess ammonium acetate in methanol (100 mL) was heated for 24 hours and resulted in Ligands 1-8. The crude product that was produced by this approach was filtered from the solution mixture, washed with water and cold methanol, and purified by column chromatography (silica gel, n-hexane/$CHCl_3$=9:1 as eluent).

In another example, 3-acetylisoqulinoline was prepared from 3-hydroxyisoquinoline using a Heck reaction, as, described in J. Y. Legros at al., *Tetrahedron* 57: 2507(20011), for example. 1-(2-oxo-2-(3'-isoquinolinyl)ethyl)pyridinium iodide was prepared by heating 3-acetylisoquinoline with excess $I_2$ in pyridine for 2 hours (R. G. Pearson, *J. Am. Chem. Soc.* 69, 3100 (1947); L. C. King et al., J. Am. Chem. Soc. 70, 239 (1948)). 3-dimethylamino-1-(2'-naphthyl)-propanone hydrochloride salt was synthesized by refluxing 2-acetyl-naphthalene, pamformaldehyde and dimethylamine hydrochloride in the presence of conc. HCl in 95% ethanol for 24 hours (F. F. Blicke et al., *J. Am. Chem. Soc.* 64, 451 (1942)). A, β-unsaturated ketone was prepared according to the approach described in, for example, (G. W. V. Cave at al., *J. Chem. Soc., Perkin Trans.* 1, 3258 (2001); F. Neve et al., [*norg. Chem.* 36, 6150 (1997)).

Representative examples of the platinum(II) complexes (Complexes 1-8) based at least in part on Structure I and Structure II are shown below:

Complex 1

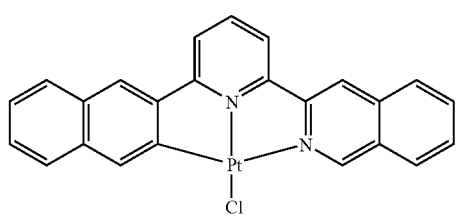

Complex 2

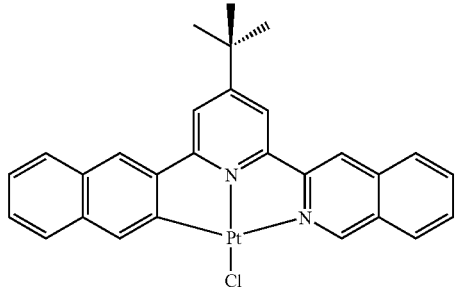

Complex 3

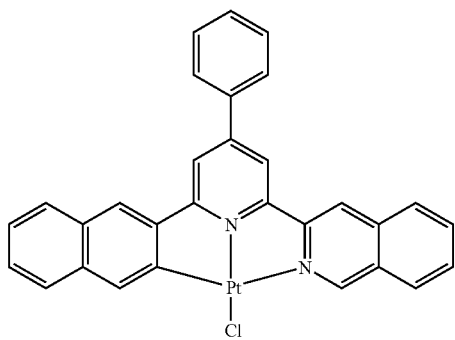

Complex 4

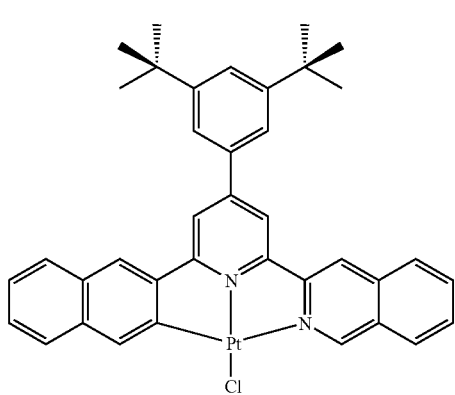

Complex 5

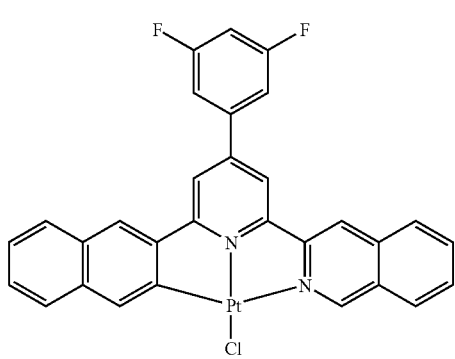

-continued

Complex 6

Although claimed subject matter is not limited in this respect, one embodiment of a method for effectively preparing neural, mononuclear platinum(II) complexes with corresponding Ligands 1-8 in the representative examples is described below. For example, a mixture of potassium tetrachloroplatinate ($K_2PtCl_4$) and the corresponding Ligand, in glacial acetic acid is refluxed for 24 hours to provide Complexes 1-8 in a yellow suspension. The yellow solid is washed with water and acetone, and recrystallized in $CH_2Cl_2$ (for Complexes 1, 3 and 4) or DMF (for Complexes 2 and 5-8). Reaction I below, for example, illustrates the use of acetic acid as a solvent in forming neural, mononuclear platinum(II) complexes for this particular embodiment.

Reaction I

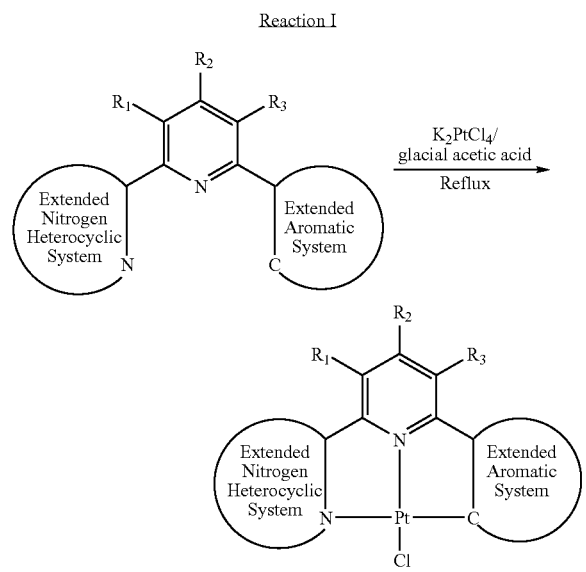

In one embodiment, for example, a tridentate ligand-bearing organometallic complex may be incorporated into a main polymer chain which may be use as emitting material in polymer light emitting device (PLED). In one embodiment, for example, a light-emitting layer of a OLED and WOLED device may comprise a host material and one or more guest materials for emitting light. At least one of the guest materials may include an organometallic complex comprising a platinum(II) complex of Structure I or Structure II. In such an embodiment, light-emitting guest material(s) may be present in an amount less than the amount of host materials and may typically be present in an amount between 1 to 20 wt % of the host. For convenience, the organometallic complex guest material may be referred to herein as an EL material. An EL material of Structure I or Structure II may have a molecular weight below 1000, but it may also comprise an oligomer or a polymer having a main chain or a side chain of repeating units having the moiety represented by Structure I or Structure II. It may be provided as a discrete material dispersed in the host material, or it may be bonded in some way to the host material such as, covalently bonded into a polymeric host, for example.

Figure 2:
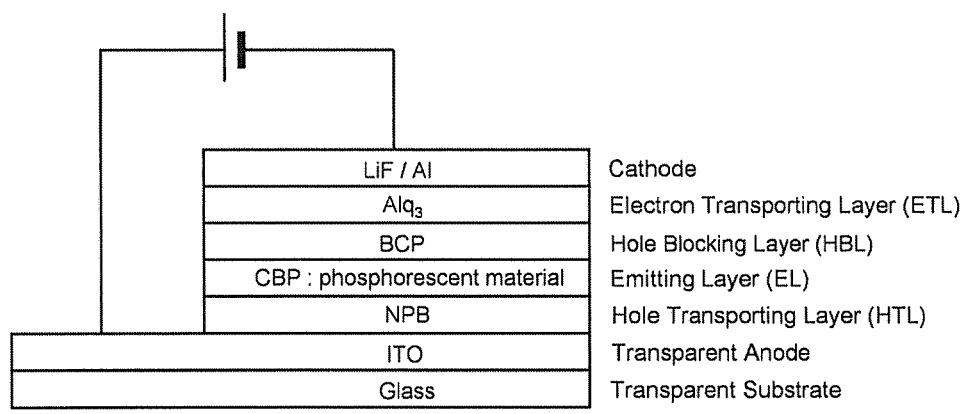
FIG. 2 is a schematic diagram illustrating an embodiment of a multi-layer hetero-structure OLED.

OLEDs, as an example, using the EL materials described herein, may possess the example embodiment multi-layer heterostructure shown in FIG. 2. This is merely an example. However, SEL materials with Structure I or Structure II may possess relatively high PL quantum yield and thermal stability, yet they may be sublimed in a vacuum. These properties render them suitable for applications in OLEDs.

For example, an OLED was prepared on a patterned indium-tin-oxide (ITO) glass with a sheet resistance of 20Ω/☐. Thermal vacuum deposition of the materials was carried out sequentially under a vacuum of $1 \times 10^{-6}$ torr in a thin film deposition system (here, a MBraun three-glove boxes system integrated with an Edwards Auto 306 and spin coater instrument). NPB (N,N'-di-1-naphthyl-N,N'-diphenyl-benzidine) was used as a hole transporting layer and $Alq_3$ (tris(8-quinolinato)aluminum or $BAlq_3$ (Bis(2-methyl-8-quinolinolato) (4-phenylphenolato)aluminum) was used as an electron transporting layer. BCP (2,9-dimethyl-4,7-diphenyl-1,10-phenanthroline, bathocuproine) was used to confine excitons within the luminescent zone. Aluminum was applied as the cathode. Selected phosphorescent Pt(II) materials were doped into a conductive host material CBP (4,4'-N,N'-dicarbazole-biphenyl) as a phosphorescent emitter. Doping levels were adjusted between 1 to 6% and electroluminescence from the Pt(II) complexes was observed. The devices were encapsulated using anodized aluminum caps and their performance was examined using Photoresearch PR-650. The current-voltage characteristics were studied using a Keithley 2400 sourcemeter.

In another particular example, an OLED, here referred to as OLED A, employing Complex 1, had the following configuration: ITO/NPB (70 nm)/CBP: Complex 1, 5%, (30 nm)/BCP (15 nm)/$Alq_3$ (30 nm)/LiF (0.3 nm)/Al (130 nm). OLED A was observed to be yellow-green light emitting with CIE coordination at 0.37, 0.58; strong emission was observed with peak maxima at 532 and 570 nm and with a shoulder at ~610 nm. A brightness of 1 cd m$^{-2}$ was obtained at 5 V. The maximum brightness of 37400 cd m$^{-2}$ was achieved at 20 V, and the maximum current efficiency of 15.4 cd A$^{-1}$ was reached at 0.2 mA cm$^{-2}$. The peak external quantum efficiency of OLED A was achieved at 14%.

In another example, OLEDs B and C were prepared in the following configuration: ITO/NPB (40 nm)/CBP: Complex 4, X %, 30 nm)/$BAlq_3$ (10 nm)/$Alq_3$ (30 nm)/LiF (0.1 nm)/Al (200 nm), where for OLED B (X=1%) and for OLED C (X=3%). These devices were also observed as emitting yellowish green light with similar CIE coordinates (OLED B: 0.36, 0.54; OLED C, 0.38, 0.55). The EL $\lambda_{max}$ (540, 592 nm with a shoulder at ~640 nm) is independent of the doping concentrations for Complex 4. OLED B gave a brightness of 1 cd m$^{-2}$ at 5 V, and a maximum current efficiency of 12.5 cd A$^{-1}$ was obtained at 1.8 mA cm$^{-2}$, and the efficiency was attained at 5 cd A$^{-1}$ if the current density was increased to 600 mA cm$^{-2}$. A maximum brightness of 63000 cd m$^{-2}$ was achieved at 20 V; this is higher than those yellow to yellowish green OLEDs employing the 6-phenyl-2,2'-bipyridyl parent congener, [(C^N^N)PtR] (maximum luminance=7800 cd m$^{-2}$, $\lambda_{max}$=564 nm; *Chem. Commun.*, 206 (2002)), [Pt(N$_2$O$_2$)] (4480 cd m$^{-2}$, CIE x=0.42, y=0.56, *Chem. Eur. J.* 9: 1263 (2003)), Pt Schiff base complexes (23000 cd m$^{-2}$, CIE x=0.48, y=0.52, *Chem. Commum.*, 1484 (2004)), [(O^N^N)PtCl] ((O^N^N)=derivatives of 6-(2-hydroxy-phenyl)-2,2'-bipyridyl, maximum luminance=37000 cd m$^{-2}$, CIE x=0.48, 0.51, *Inorg. Chem.*, 44: 4442 (2005)), [(X-bt)Pt(acac)] (11320 cd m$^{-2}$ at 14 V, CIE x=0.47, 0.51, X-bt=substituted 2-phenylbenzothiazolato, X=H or F, acac=acetylacetonate, *Polyhedron*, 24: 881 (2005)), [Pt(N^N)$_2$] ((N^N)=3-trifluoromethyl-5-(2-pyridyl)pyrazole, maximum luminance=41000 cd m$^{-2}$, CIE x=0.42, y=0.53, *Inorg. Chem.*, 45:137 (2006)) and other non-Pt emitters as dopants (*Chem. Mater.*, 13: 456 (2001); *Synth. Met.*, 139: 671 (2003); *J. Am. Chem. Soc.*, 123: 4304 (2001)).

Figure 3:
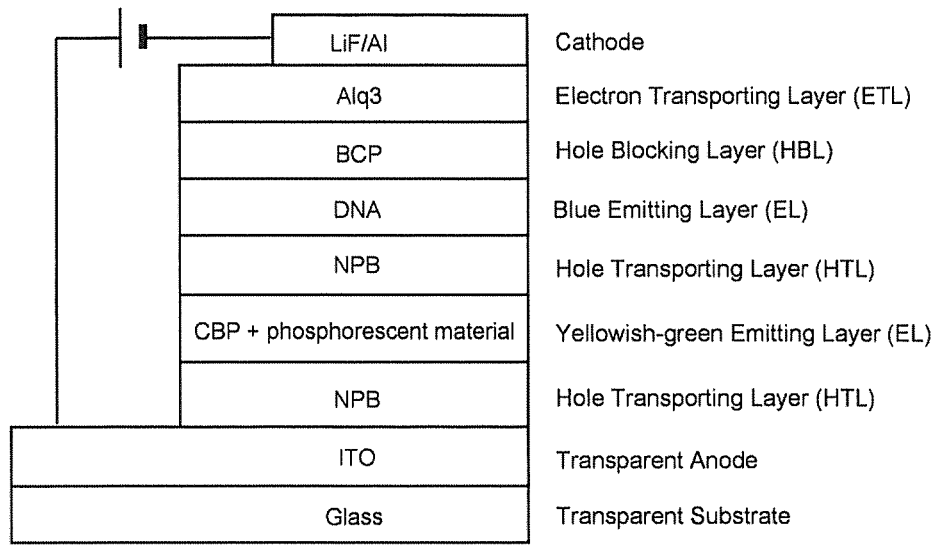
FIG. 3 is a schematic diagram illustrating an embodiment of a device structure of a WOLED.

As another example, White Organic Light-emitting devices (WOLEDs) using the phosphorescent materials described herein may possess the example embodiment multi-layer heterostructure shown in FIG. 3. Organometallic complexes of Complex 1 may possess relatively high PL quantum yield and thermal stability, yet they may be sublimed in a vacuum. Organic layers were deposited by high-vacuum (10$^{-6}$ Torr) thermal evaporation onto a cleaned glass substrate pre-coated with transparent, conductive indium tin oxide (ITO). A 30 nm-thick film of NPB served as a hole-transporting layer (HTL). A 10 nm-thick light-emitting layer (EML) comprising a CBP host was deposited while being doped with different wt.-% Complex 1 or Complex 6. The doping level was controlled by the deposition rates. Introduction of such a thin layer is to reduce operational voltage. A 2 nm thick layer of DNA was used as a blue light emission layer and a 4 nm thick layer of BCP was used to confine excitons in the EML. A 30 nm-thick layer of tris-(8-hydroxy-quinoline) aluminum (Alq3) was used to transport and inject electrons into the EML. A shadow mask with a 3×3 mm$^2$ opening was used to define the cathode comprising a 0.3 nm-thick layer of LiF and a 130 nm thick aluminum cap.

In addition, a relatively high efficiency white organic light-emitting device (WOLED) has been demonstrated with phosphorescent/fluorescent dual emitting layer. By employing a fluorescent host DNA as a blue-emitting source and a Pt(II) complex, Complex 1 (5%-wt in CBP), as a yellow-green light source, a balanced white light emission was obtained. WOLED A shows a maximum brightness of 38200 cd m$^{-2}$ at 15.5 V with CIE coordination at 0.33, 0.39. The peak external quantum efficiency and current efficiency are 11%, and 12.6 lm W$^{-1}$, respectively. At the benchmark brightness of 100 cd m$^{-2}$, the external quantum efficiency and current efficiency are 10.1% and 10.6 lm W$^{-1}$, respectively.

In another embodiment, WOLED B was produced by employing a fluorescent host DNA as a blue-emitting source and a Pt(II) complex, Complex 6 (6.3%-wt in CBP), as a yellow light source, to obtain a balanced white light emission. WOLED B shows a maximum brightness of 24900 cd m$^{-2}$ at 13.5 V with CIE coordination at 0.32, 0.35. The peak external quantum efficiency and current efficiency are 4.01%, and 4.25 lm W$^{-1}$, respectively. At the benchmark brightness of 1210 cd m$^{-2}$, the external quantum efficiency and current efficiency are 3.36% and 2.66 lm W$^{-1}$, respectively.

Figure 26:
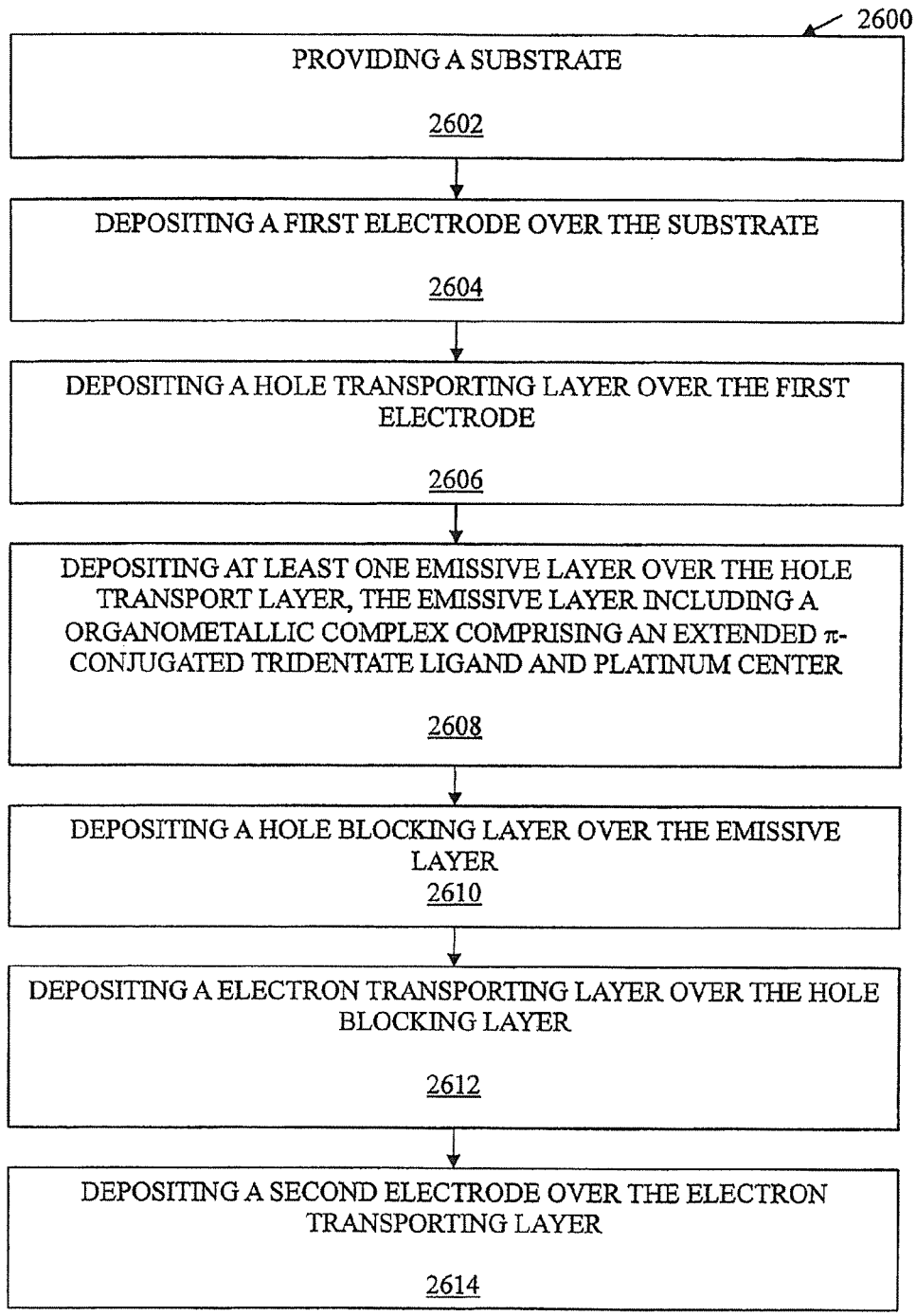
FIG. 26 is a flow chart of one embodiment of a procedure for preparing a light-emitting device.

Referring to FIG. 26, a flow diagram is provided to illustrate an example embodiment of a procedure to prepare a light-emitting device. As illustrated, procedure embodiment 2600 starts at 2602 in which a substrate may be employed. At 2604, a first electrode may be deposited over the substrate. At 2606, a hole transporting layer may be deposited over the first electrode. At 2608, at least one emissive layer may be deposited over the hole transport layer. The emissive layer may comprise at least one host material and/or one emitting/dopant complex. The emitting/dopant complex of the emissive layer may comprise an organometallic complex, for example, as disclosed herein, such as an extended π-conjugated tridentate ligand and a platinum center, for example. At 2610, a hole blocking layer may be deposited over the emissive layer. At 2612, an electron transporting layer may be deposited over the hole blocking layer. At 2614, a second electrode may be deposited over the electron transporting layer. Procedure embodiment, 2600, as described above may be utilized, for example, to prepare a light-emitting device, such as an embodiment of a multi-layer heterostructure OLED.

Figure 27:
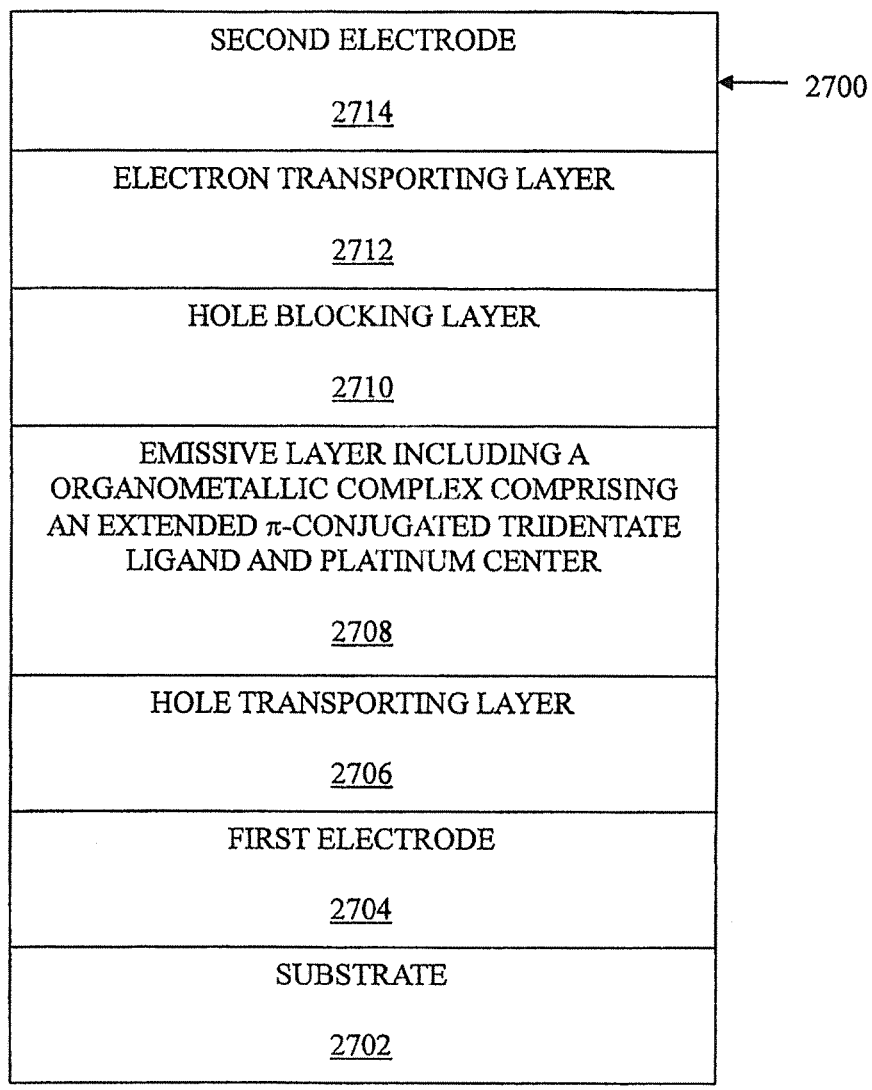
FIG. 27 is a schematic diagram illustrating an embodiment of a multi-layer hetero-structure OLED.

Referring to FIG. 27, a schematic diagram illustrates an example embodiment of a multi-layer heterostructure OLED 2700.

As shown in FIG. 27, multi-layer heterostructure OLED 2700 may include a first electrode 2704 deposited over substrate 2702. A hole transporting layer 2706 may be deposited over first electrode 2704. An emissive layer 2708 may be deposited over hole transporting layer 2706. Emissive layer 2708 may comprise at least a host material and/or a(n) emitting/dopant complex. The emitting/dopant complex of emissive layer 2708 may comprise an organometallic complex as disclosed herein, such as an extended π-conjugated tridentate ligand and a platinum center. A hole blocking layer 2710 may be deposited over emissive layer 2708. An electron transporting layer 2712 may be deposited over hole blocking layer 2710. A second electrode 2714 may be deposited over electron transporting layer 2712. Second electrode 2714 may sandwich hole transporting layer 2706, emissive layer 2708, hole blocking layer 2710 and electron transporting layer 2712 between first electrode 2704 and second electrode 2714. Multi-layer heterostructure OLED 2700, as shown in FIG. 27, may be incorporated in a variety of devices such as, for example, without limitation, flat panel displays, lighting sources, and/or the like.

Figure 28:
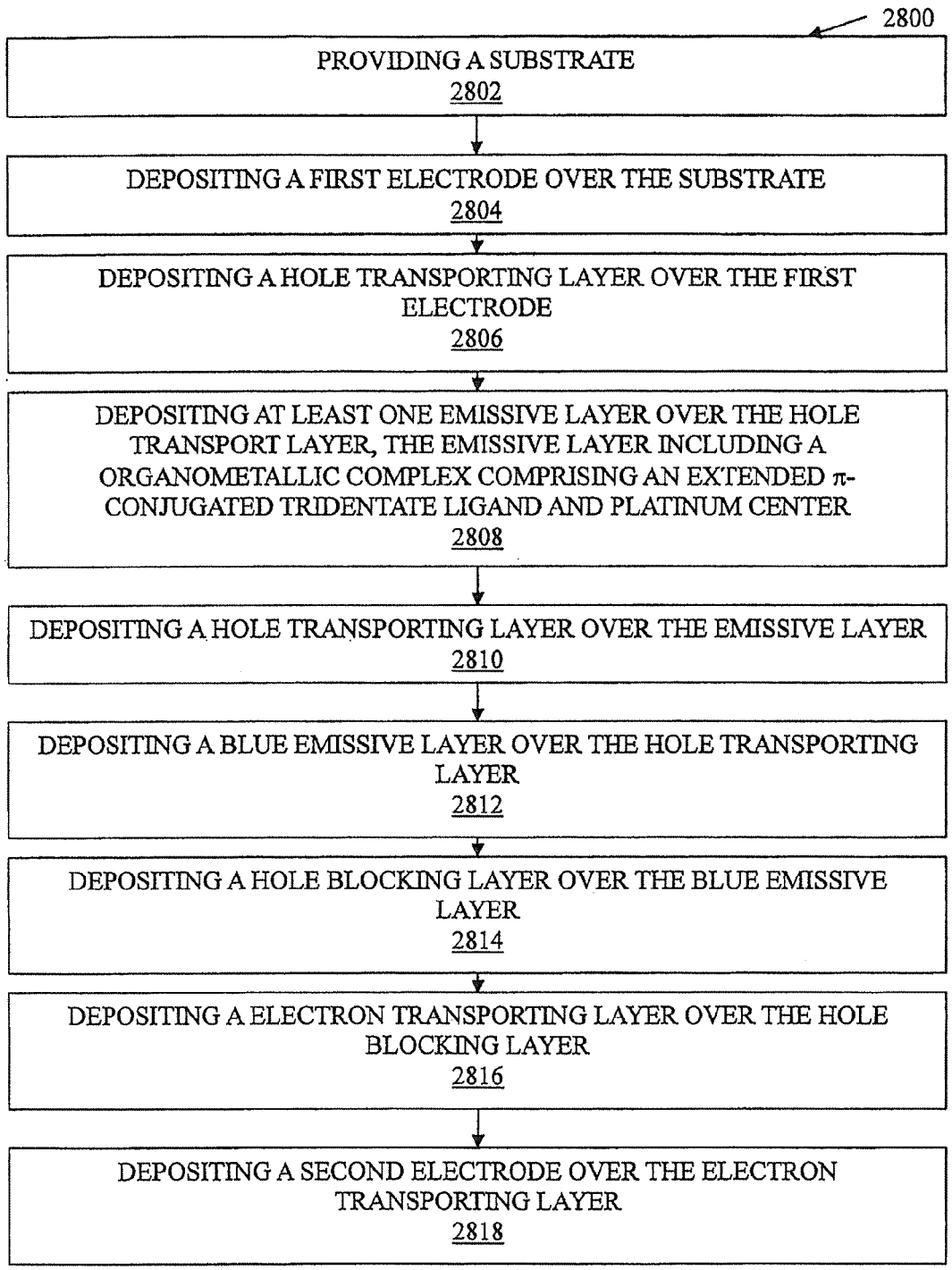
FIG. 28 is a flow chart of another embodiment of a procedure for preparing a light-emitting device.

Referring to FIG. 28, a flow diagram is provided to illustrate an example embodiment of a procedure to prepare a light-emitting device. As illustrated, procedure embodiment 2800 starts at 2802 in which a substrate may be employed. At 2804, a first electrode may be deposited over the substrate. At 2806, a hole transporting layer may be deposited over the first electrode. At 2808, at least one emissive layer may be deposited over the hole transport layer. The emissive layer may comprise at least one host material and/or one emitting/dopant complex. The emitting/dopant complex of the emissive layer may comprise an organometallic complex, for example, as disclosed herein, such as an extended π-conjugated tridentate ligand and a platinum center, for example. At 2810, a hole blocking layer may be deposited over the emissive layer. At 2812, a blue emissive layer may be deposited over the hole blocking layer. At 2814, a hole blocking layer may be deposited over the blue emissive layer. At 2816, an electron transporting layer may be deposited over the hole blocking layer. At 2818, a second electrode may be deposited over the electron transporting layer. Procedure embodiment, 2800, as described above may be utilized, for example, to prepare a light-emitting device, such as an embodiment of a multi-layer heterostructure WOLED, for example.

Figure 29:
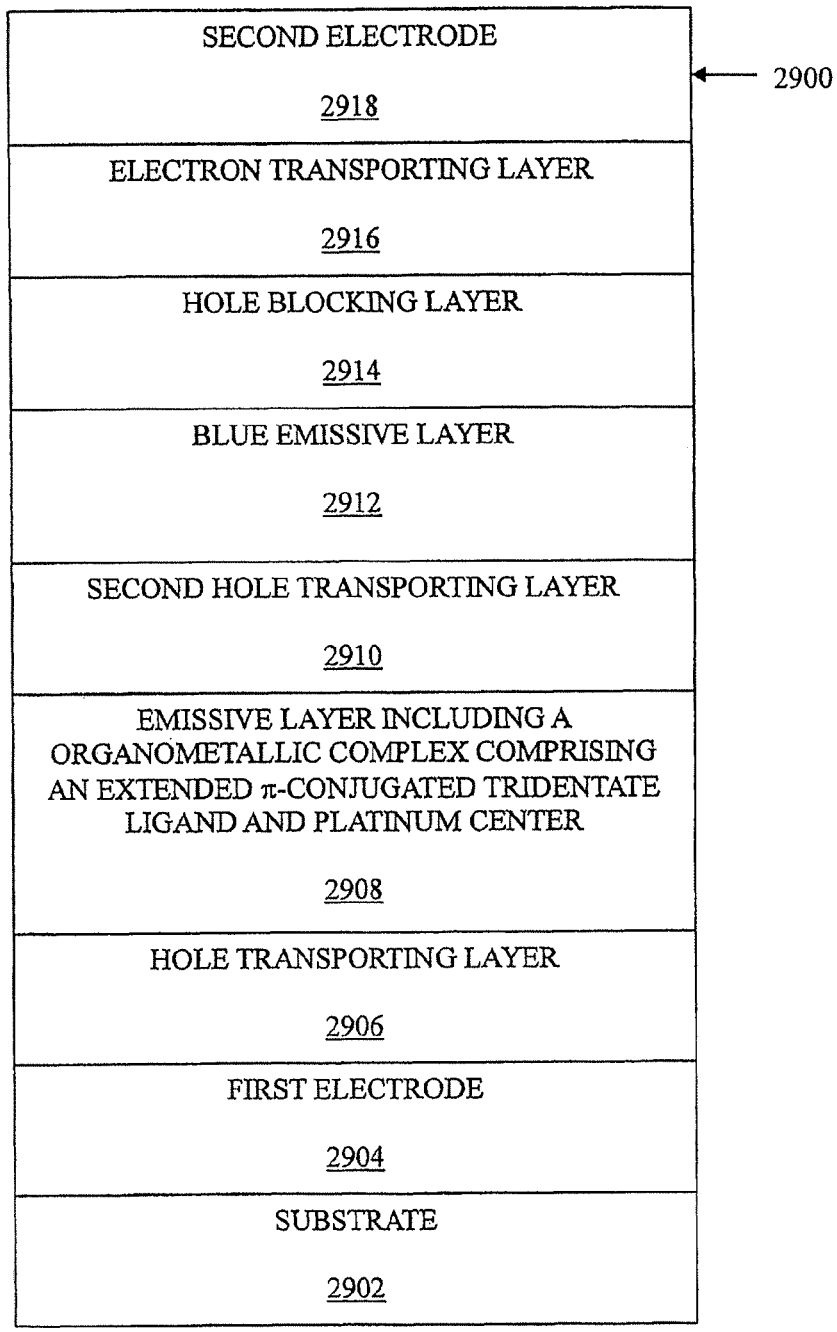
FIG. 29 is a schematic diagram illustrating another embodiment of a multi-layer hetero-structure OLED.

Referring to FIG. 29, a schematic diagram illustrates an example embodiment of a multi-layer heterostructure WOLED 2900. As shown in FIG. 29, WOLED 2900 may include a first electrode 2904 deposited over substrate 2902. A hole transporting layer 2906 may be deposited over first electrode 2904. A first emissive layer 2908 may be deposited over hole transporting layer 2906. First emissive layer 2908 may comprise at least a host material and/or a(n) emitting/dopant complex. The emitting/dopant complex of first emissive layer 2908 may comprise an organometallic complex as disclosed herein, such as an extended π-conjugated tridentate ligand and a platinum center, for example. A second hole transporting layer 2910 may be deposited over emissive layer 2908. A blue emissive layer 2912 may be deposited over hole transporting layer 2910. A hole blocking layer 2914 may be deposited over blue emissive layer 2912. An electron transporting layer 2916 may be deposited over hole blocking layer 2914. A second electrode 2918 may be deposited over electron transporting layer 2916. Second electrode 2918 may sandwich hole transporting layer 2906, first emissive layer 2908, second hole transporting layer 2910, blue emissive layer 2912, hole blocking layer 2914, and electron transporting layer 2916 between first electrode 2904 and second electrode 2918. WOLED 2900, as shown in FIG. 29, may be incorporated in a variety of devices such as, for example, without limitation, flat panel displays, lighting sources, and/or the like.

EXAMPLES

A number of example embodiments are provide below, although it is not intended that claimed subject matter be limited to these particular example embodiment.

Example 1

Example 1 describes the synthesis of Ligand 1 and complex 1:
(a) The Synthesis Method and Physical Characterizations of Ligand 1:

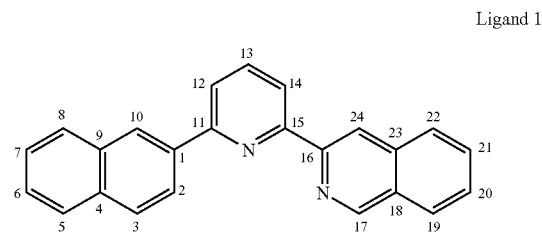 [SMILES: c1cc(-c2ccc3ccccc3c2)nc(-c2cc3ccccc3cn2)c1]

Ligand 1

3-acetylisoqulinoline was prepared from 3-hydroxyisoqulinoline using a Heck reaction (J. Y. Legros et al., *Tetrahedron* 57: 2507 (2001)). 1-(2-oxo-2-(3'-isoquinolinyl)ethyl)pyridinium iodide was prepared by heating 3-acetylisoqulinoline with excess 12 in pyridine for 2 hours (R. G. Pearson, *J. Am. Chem. Soc.* 69, 3100 (1947); L. C. King et al., *J. Am. Chem. Soc.* 70, 239 (1948)). 3-dimethylamino-1-(2'-naphthyl)-propanone hydrochloride salt was synthesized by refluxing 2-acetylnaphthalene, paraformaldehyde and dimethylamine hydrochloride in the presence of conc. HCl in 95% ethanol for 24 hours (F. F. Blicke et al., *J. Am. Chem. Soc.* 64, 451 (1942)).

Heating 1-(2-oxo-2-(3'-isoquinolinyl)ethyl)pyridinium iodide (1.00 g, 2.66 mmol), 3-dimethylamino-I-(2' naphthyl)-propanone hydrochloride salt (0.70 g, 2.7 mmol) and ammonium acetate (5.00 g, 64.9 mmol) in methanol (100 mL) for 24 hours gave crude Ligand 1. The crude product was filtered from the solution mixture, washed with water and cold methanol, and purified by column chromatography (silica gel, n-hexane/CHC13=9:1 as eluent) to afford Ligand 1 as off-white solid. Yield: 0.53 g, 60%.

Ligand 1: $^1$H NMR (300 MHz, CDCl$_3$, 25° C., TMS): δ 7.5-7.6 (m, 2H; H$^6$ and H$^7$), 7.7 (t, $^3$J(H,H)=8 Hz, 1H; H$^{21}$), 7.8 (t, $^3$J(H,H)=9 Hz, 1H; H$^{20}$), 7.9-8.1 (m, 7H; H$^3$, H$^5$, H$^8$, H$^{12}$, H$^{13}$, H$^{19}$ and H$^{22}$), 8.4 (dd, $^4$J(H,H)=2 Hz, $^3$J(H,H)=10 Hz, 1H; H$^2$), 8.5 (dd, $^4$J(H,H)=1 Hz, $^3$J(H,H)=9 Hz, 1H; H$^{14}$), 8.7 (s, 1H; H$^{10}$), 9.1 (s, 1H; H$^{24}$), 9.4 (s, 1H; H$^{17}$); MS (70 eV, EI): m/z: 332 [M$^+$].

(b) The Synthesis Method and Physical Characterizations of Complex 1:

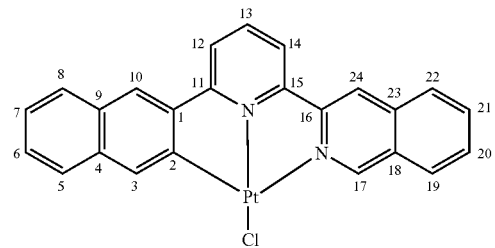

Complex 1

A mixture of K$_2$PtCl$_4$ (0.22 g, 0.30 mmol) and Ligand 1 (0.10 g, 0.30 mmol) in glacial acetic acid (100 mL) was refluxed for 24 hours affording crude Complex 1 in a yellow suspension. The yellow solid was washed with water and acetone, and recrystallized in CH$_2$Cl$_2$. Ligand 1 was isolated as a yellow crystalline solid. Yield: 0.13 g, 80%.

Figure 4:
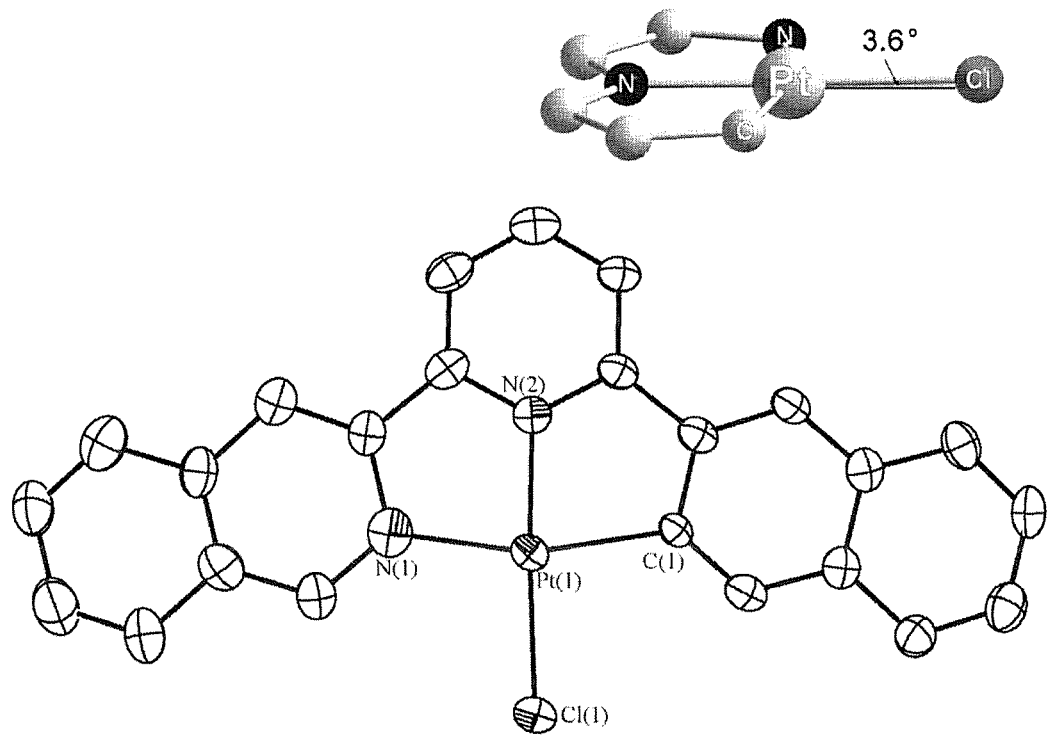
FIG. 4 is a schematic diagram illustrating an X-ray structure for an embodiment of an organic complex, here complex 1.

Complex 1: The X-ray crystal structure for Complex 1 is depicted in FIG. 4, which shows that the coordinating O, N, Pt and Cl atoms in Complex 1 are closely co-planar (with the Cl atom being out of plane by only 3.6°). $^1$H NMR (400 MHz, d$_7$-DMF, 25° C., TMS): δ 7.4 (t, $^3$J(H,H)=7 Hz, 1H; H$^6$), 7.5 (t, $^3$J(H,H)=7 Hz, 1H; H$^7$), 7.8 (d, $^3$J(H,H)=9 Hz, 1H; H$^8$), 7.9 (d, $^3$J(H,H)=9 Hz, 1H; H$^5$), 8.0 (t, $^3$J(H,H)=7 Hz, 1H; H$^{21}$), 8.1-8.2 (m, 2H; H$^3$ and H$^{20}$), 8.2-8.3 (m, 2H; H$^{14}$ and H$^{19}$), 8.3-8.4 (m, 3H; H$^{10}$, H$^{12}$ and H$^{13}$), 8.6 (t, $^3$J(H,H)=8.5 Hz, 1H; H$^{22}$), 9.2 (s, 1H; H$^{24}$), 9.8 (s, 1H; H$^{17}$); MS (+FAB): m/z: 562 [M$^+$]; elemental analysis calcd (%) for C$_{24}$H$_{15}$ClN$_2$Pt (561.9): C, 51.30; H, 2.69; N, 4.99. found: C, 51.10; H, 2.69; N, 4.99.

Example 2

Example 2 describes the synthesis of Ligand 2 and Complex 2:
(a) The Synthesis Method and Physical Characterizations of Ligand 2:

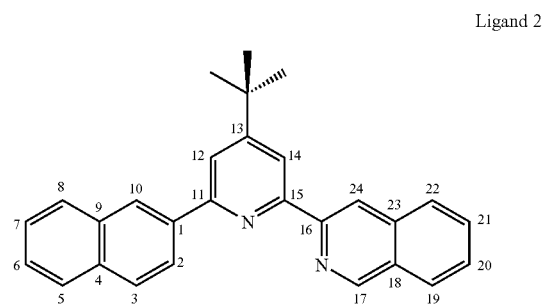

Ligand 2

3-acetylisoqulinoline was prepared from 3-hydroxyisoqulinoline using Heck reaction (J. Y. Legros et al., *Tetrahedron* 57: 2507 (2001)). 1-(2-oxo-2-(3'-isoquinolinyl)ethyl) pyridinium iodide was prepared by heating 3-acetylisoqulinoline with excess 12 in pyridine for 2 hours (R. G. Pearson, *J. Am. Chem. Soc.* 69, 3100 (1947); L. C. King et al., *J. Am. Chem. Soc.* 70, 239 (1948)). α,β-unsaturated ketone (tert-butylidene-2-acetonaphthone) was prepared according to the approach described in G. W. V. Cave et al., *J. Chem. Soc., Perkin Trans.* 1, 3258 (2001); F. Neve et al., *Inorg. Chem.* 36, 6150 (1997), for example.

Heating 1-(2-oxo-2-(3'-isoquinolinyl)ethyl)pyridinium iodide (0.47 g, 1.3 mmol), tert-butylidene-2-acetonaphthone (0.30 g, 1.3 mmol) and ammonium acetate (5.00 g, 64.9 mmol) in methanol (100 mL) for 24 hours gave crude Ligand 2. The crude product was filtered from the solution mixture, washed with water and cold methanol, and purified by column chromatography (silica gel, n-hexane/CHCl$_3$=9:1 as eluent) to afford Ligand 2 as off-white solid. Yield: 0.27 g, 55%.

Ligand 2: $^1$H NMR (300 MHz, CDCl$_3$, 25° C., TMS): δ 1.5 (s, 9H; C(CH$_3$)$_3$), 7.3-7.6 (m, 2H; H$^6$ and H$^7$), 7.6 (t, $^3$J(H,H)=8 Hz, 1H; H$^{21}$), 7.7 (t, $^3$J(H,H)=8 Hz, 1H; H$^{20}$), 7.9 (m, 2H; H$^5$ and H$^{12}$), 8.0-8.1 (m, 4H; H$^3$, H$^8$, H$^{19}$ and H$^{22}$), 8.4 (dd, $^4$J(H,H)=2 Hz, $^3$J(H,H)=5 Hz, 1H; H$^2$), 8.6 (d, $^4$J(H,H)=1.6 Hz, 1H; H$^{14}$), 8.6 (s, 1H; H$^{10}$), 9.1 (s, 1H; H$^{24}$), 9.4 (s, 1H; H$^{17}$); MS (70 eV, EI): m/z: 388 [M$^+$].

(b) The Synthesis Method and Physical Characterizations of Complex 2:

Complex 2

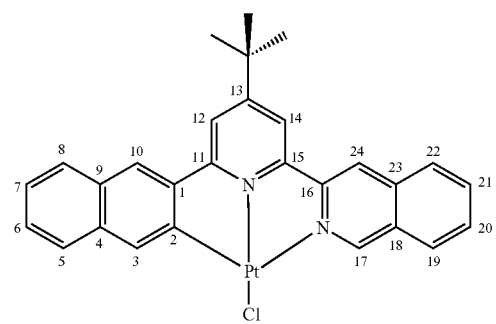

A mixture of K$_2$PtCl$_4$ (1.49 g, 3.58 mmol) and Ligand 2 (1.39 g, 3.58 mmol) in glacial acetic acid (100 mL) was refluxed for 24 hours affording crude Complex 2 in a yellow suspension. The yellow solid was washed with water and acetone, and recrystallized in DMF. Complex 2 was isolated as a yellow crystalline solid. Yield: 1.90 g, 85.9%.

Complex 2: $^1$H NMR data were not available due to the low solubility of Complex 2 in various deuterated solvents. MS (+FAB): m/z: 618 [M$^+$]; elemental analysis calcd (%) for C$_{28}$H$_{23}$ClN$_2$Pt (618.0): C, 54.42; H, 3.75; and N, 4.53. found: C, 52.74; H, 3.95; and N, 4.60.

Example 3

Example 3 describes the synthesis of Ligand 3 and Complex 3:
(a) The Synthesis Method and Physical Characterizations of Ligand 3:

Ligand 3

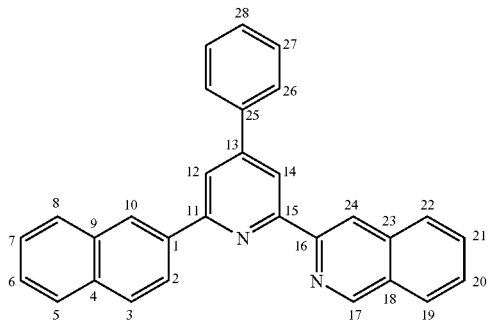

3-acetylisoqulinoline was prepared from 3-hydroxyisoqulinoline using a Heck reaction (J. Y. Legros et al., *Tetrahedron* 57: 2507 (2001)). 1-(2-oxo-2-(3'-isoquinolinyl)ethyl) pyridinium iodide was prepared by heating 3-acetylisoqulinoline with excess 12 in pyridine for 2 hours (R. G. Pearson, *J. Am. Chem. Soc.* 69, 3100 (1947); L. C. King et al., *J. Am. Chem. Soc.* 70, 239 (1948)). α,β-unsaturated ketone (benzylidene-2-acetonaphthone) was prepared according to the approach described in G. W. V. Cave et al., *J. Chem. Soc., Perkin Trans.* 1, 3258 (2001); F. Neve et al., *Inorg. Chem.* 36, 6150 (1997), for example.

Heating 1-(2-oxo-2-(3'-isoquinolinyl)ethyl)pyridinium iodide (1.00 g, 2.66 mmol), benzylidene-2-acetonaphthone (0.69 g, 2.7 mmol) and ammonium acetate (5.00 g, 64.9 mmol) in methanol (100 mL) for 24 hours gave crude Ligand 3. The crude product was filtered from the solution mixture, washed with water and cold methanol, and purified by column chromatography (silica gel, n-hexane/CHCl$_3$=9:1 as eluent) to afford Ligand 3 as off-white solid. Yield: 0.87 g, 80%.

Ligand 3: $^1$H NMR (400 MHz, CDCl$_3$, 25° C., TMS): δ 7.5 (t, $^3$J(H,H)=6 Hz, 1H; H$^{28}$), 7.5-7.6 (m, 4H; H$^5$, H$^7$ and H$^{27}$), 7.7 (t, 3J(H,H)=8 Hz, 1H; H$^{21}$), 7.8 (t, $^3$J(H,H)=8 Hz, 1H; H$^{20}$), 7.9-8.0 (m, 3H; H$^8$ and H$^{26}$), 8.0-8.1 (m, 4H; H$^3$, H$^6$, H$^{19}$ and H$^{22}$), 8.1 (s, 1H; H$^{12}$), 8.5 (d, $^3$J(H,H)=5 Hz, 1H; H$^2$), 8.7 (s, 1H; H$^{10}$), 8.8 (s, 1H; H$^{14}$), 9.1 (s, 1H; H$^{24}$), 9.4 (s, 1H; H$^{17}$); MS (70 eV, EI): m/z: 408 [M$^+$].

(b) The Synthesis Method and Physical Characterizations of Complex 3:

Complex 3

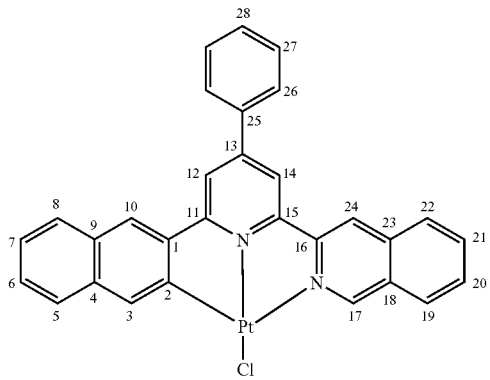

A mixture of K$_2$PtCl$_4$ (0.52 g, 1.3 mmol) and Ligand 3 (0.51 g, 1.3 mmol) in glacial acetic acid (100 mL) was refluxed for 24 hours affording crude Complex 3 in a yellow suspension. The yellow solid was washed with water and acetone, and recrystallized in CH$_2$Cl$_2$. Complex 3 was isolated as yellow crystals. Yield: 0.72 g, 90%.

Figure 5:
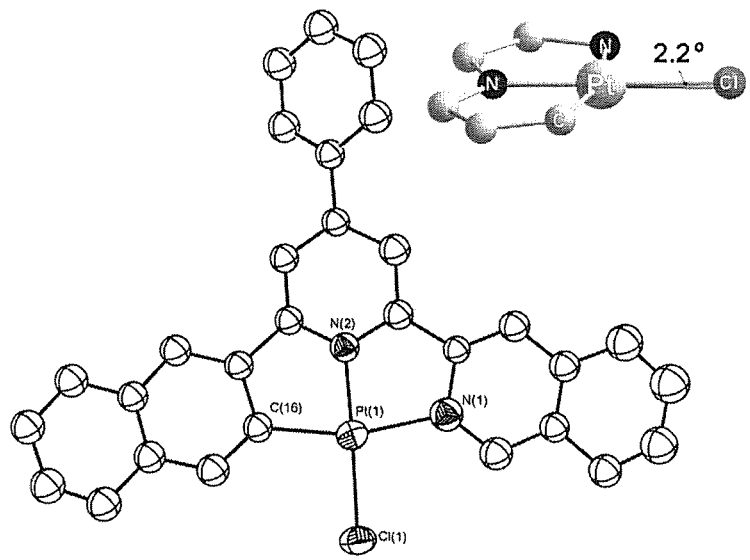
FIG. 5 is a schematic diagram illustrating an X-ray structure for an embodiment of a complex, here complex 3.

Material 3: The X-ray crystal structure for Complex 3 is depicted in FIG. 5 which shows that the coordinating O, N, Pt and Cl atoms Complex 3 are closely co-planar (with the Cl atom being out of plane by only 2.2°). $^1$H NMR (400 MHz, d$_7$-DMF, 25° C., TMS): δ 7.4 (t, $^3$J(H,H)=8 Hz, 1H; H$^6$), 7.4 (t, $^3$J(H,H)=8 Hz, 1H; H$^7$), 7.6-7.7 (m, 3H; H$^{10}$ and H$^{26}$), 7.7 (d, $^3$J(H,H)=8 Hz, 1H; H$^8$), 7.8 (d, $^3$J(H,H)=8 Hz, 1H; H$^5$), 7.9 (t, $^3$J(H,H)=7 Hz, 1H; H$^{21}$), 8.0 (t, $^3$J(H,H)=8 Hz, 1H; H$^{20}$), 8.1 (d, $^3$J(H,H)=8 Hz, 1H; H$^{19}$), 8.2 (m, 3H; H$^{27}$ and H$^{28}$) 8.4-8.5 (m, 2H; H$^{14}$ and H$^{22}$), 8.6 (s, 1H; H$^{12}$), 9.3 (s, 1H; H$^{24}$), 9.7 (s, 1H; H$^{17}$); MS (+FAB): m/z: 638 [M$^+$]; elemental analysis calcd (%) for C$_{30}$H$_{19}$ClN$_2$Pt (638.0): C, 56.48; H, 3.00; N, 4.39. found: C, 56.04; H, 3.02; N, 4.50.

Example 4

Example 4 describes the synthesis of Ligand 4 and Complex 4:
(a) The Synthesis Method and Physical Characterizations of Ligand 4:

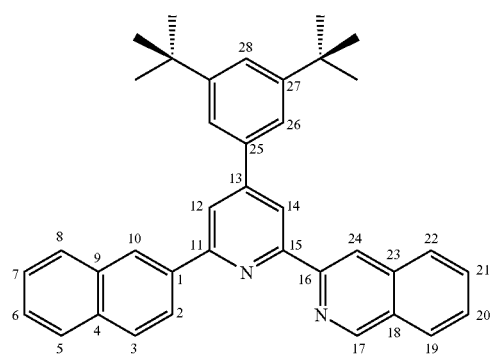

Ligand 4

3-acetylisoqulinoline was prepared from 3-hydroxyisoqulinoline using a Heck reaction (J. Y. Legros et al., *Tetrahedron* 57: 2507 (2001)). 1-(2-oxo-2-(3'-isoquinolinyl)ethyl) pyridinium iodide was prepared by heating 3-acetylisoqulinoline with excess 12 in pyridine for 2 hours (R. G. Pearson, *J. Am. Chem. Soc.* 69, 3100 (1947); L. C. King et al., *J. Am. Chem. Soc.* 70, 239 (1948)). α,β-unsaturated ketone 3',5'-di-tert-butylbenzylidene-2-acetonaphthone) was prepared according to the approach described in G. W. V. Cave et al., *J. Chem. Soc., Perkin Trans.* 1, 3258 (2001); F. Neve et al., *Inorg. Chem.* 36, 6150 (1997), for example.

Heating 1-(2-oxo-2-(3'-isoquinolinyl)ethyl)pyridinium iodide (0.90, 2.4 mmol), 3',5'-di-tert-butylbenzylidene-2-acetonaphthone (0.89 g, 2.4 mmol) and ammonium acetate (5.00 g, 64.9 mmol) in methanol (100 mL) for 24 hours gave crude Ligand 4. The crude product was filtered from the solution mixture, washed with water and cold methanol, and purified by column chromatography (silica gel, n-hexane/CHCl$_3$=9:1 as eluent) to afford Ligand 4 as white solid. Yield: 0.89 g, 72%.

Ligand 4: $^1$H NMR (400 MHz, CDCl$_3$, 25° C., TMS): δ 1.5 (s, 18H; C(CH$_3$)$_3$), 7.6-7.7 (m, 6H; H$^6$, H$^8$, H$^{21}$, H$^{26}$ and H$^{28}$), 7.8 (t, $^3$J(H,H)=8 Hz, 1H; H$^{20}$), 7.9-8.0 (m, 1H; H$^5$), 8.0-8.1 (m, 5H; H$^3$, H$^7$, H$^{12}$, H$^{19}$ and H$^{22}$), 8.5 (d, $^3$J(H,H)=10 Hz, 1H; H$^2$), 8.7 (s, 1H; H$^{10}$), 8.8 (s, 1H; H$^{14}$), 9.1 (s, 1H; H$^{24}$), 9.4 (s, 1H; H$^{17}$); MS (70 eV, EI): m/z: 520 [M$^+$].

(b) The Synthesis Method and Physical Characterizations of Complex 4:

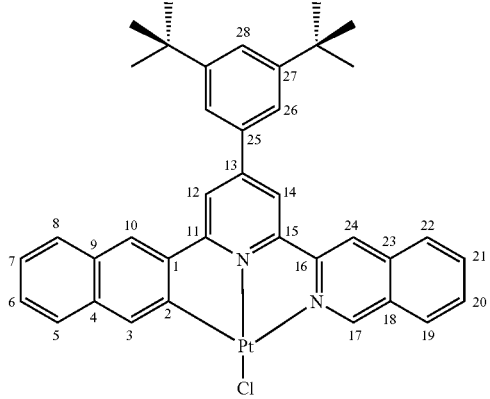

Complex 4

A mixture of K$_2$PtCl$_4$ (0.50 g, 1.2 mmol) and Ligand 4 (0.63 g, 1.2 mmol) in glacial acetic acid (100 mL) was refluxed for 24 hours affording crude Complex 4 in a yellow suspension. The yellow solid was washed with water and acetone, and recrystallized in CH$_2$Cl$_2$. Complex 4 was isolated as an orange crystalline solid. Yield: 0.73 g, 80%.

Complex 4: $^1$H NMR (400 MHz, d$_7$-DMF, 25° C., TMS): δ 7.4 (t, $^3$J(H,H)=7 Hz, 1H; H$^6$), 7.4 (t, $^3$J(H,H)=6.7 Hz, 1H; H$^7$), 7.7 (d, $^3$J(H,H)=7 Hz, 1H; H$^8$), 7.8 (m, 2H; H$^5$ and H$^{28}$), 7.9 (t, $^3$J(H,H)=7 Hz, 1H; H$^{21}$), 8.0-8.1 (m, 5H; H$^3$, H$^{19}$, H$^{20}$ and H$^{26}$), 8.4-8.5 (m, 3H; H$^{10}$, H$^{14}$ and H$^{22}$), 8.6 (s, 1H; H$^{12}$), 9.3 (s, 1H; H$^{24}$), 9.7 (s, 1H; H$^{17}$); MS (+FAB): m/z: 751 [M$^+$]; elemental analysis calcd (%) for C$_{38}$H$_{35}$ClN$_2$Pt (750.2): C, 60.84; H, 4.70; N, 3.73. found: C, 60.91; H, 4.77; N, 3.80.

Example 5

Example 5 describes the synthesis of Ligand 5 and Complex 5:
(a) The Synthesis Method and Physical Characterizations of Ligand 5:

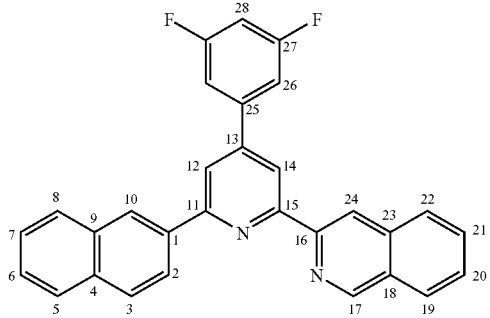

Ligand 5

3-acetylisoqulinoline was prepared from 3-hydroxyisoqulinoline using a Heck reaction (J. Y. Legros et al., *Tetrahedron* 57: 2507 (2001)). 1-(2-oxo-2-(3'-isoquinolinyl)ethyl) pyridinium iodide was prepared by heating 3-acetylisoqulinoline with excess 12 in pyridine for 2 hours (R. G. Pearson, *J. Am. Chem. Soc.* 69, 3100 (1947); L. C. King et al., *J. Am. Chem. Soc.* 70, 239 (1948)). α,β-unsaturated ketone (3',5'-difluorobenzylidene-2-acetonaphthone) was prepared according to the approach described in G. W. V. Cave et al., *J. Chem. Soc., Perkin Trans.* 1, 3258 (2001); F. Neve et al., *Inorg. Chem.* 36, 6150 (1997), for example.

Heating 1-(2-oxo-2-(3'-isoquinolinyl)ethyl)pyridinium iodide (1.91 g, 5.19 mmol), 3'5'-difluorobenzylidene-2-acetonaphthone (1.53 g, 5.19 mmol) and ammonium acetate (5.00 g, 64.9 mmol) in methanol (100 mL) for 24 hours gave crude Ligand 5. The crude product was filtered from the solution mixture, washed with water and cold methanol, and purified by column chromatography (silica gel, n-hexanclCHCl$_3$=9:1 as eluent) to afford Ligand 5 as white solid. Yield: 2.03 g, 88.1%.

Ligand 5: $^1$H NMR (400 MHz, CD$_2$Cl$_2$, 25° C., TMS): δ 7.0 (t, $^3$J(H,F)=9 Hz, 1H; H$^{28}$), 7.4-7.5 (m, 2H; H$^{26}$), 7.6 (m, 2H; H$^6$ and H$^8$), 7.7 (t, $^3$J(H,H)=8 Hz, 1H; H$^{21}$), 7.8 (t, $^3$J(H,H)=8 Hz, 1H; H$^{20}$), 8.0 (m, 1H; H$^5$), 8.0-8.1 (m, 5H; H$^3$, H$^7$, H$^{14}$, H$^{19}$ and H$^{22}$), 8.5 (d, $^3$J(H,H)=10 Hz, 1H; H$^2$), 8.7 (s, 1H; H$^{10}$), 8.8 (s, 1H; H$^{12}$), 9.1 (s, 1H; H$^{24}$), 9.4 (s, 1H; H$^{17}$); $^{19}$F NMR (376 MHz, CD$_2$Cl$_2$, 25° C.): δ −109.6 (t, $^3$J(H,F)=8 Hz); MS (70 eV, EI): m/z: 444 [M$^+$].

(b) The Synthesis Method and Physical Characterizations of Complex 5:

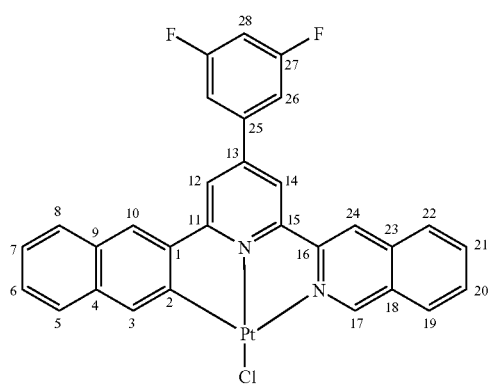

Complex 5

A mixture of K$_2$PtCl$_4$ (0.79 g, 1.9 mmol) and Ligand 5 (0.85 g, 1.9 mmol) in glacial acetic acid (100 mL) was refluxed for 24 hours affording crude Complex 5 in a yellow suspension. The yellow solid was washed with water and acetone, and recrystallized in DMF. Complex 5 was isolated as a yellow crystalline solid. Yield: 1.1 g, 88%.

Complex 5: $^1$H NMR (400 MHz, d$_7$-DMF, 25° C., TMS): δ 7.3 (t, $^3$J(H,H)=8 Hz, 1H; H$^6$), 7.3 (t, $^3$J(H,H)=8 Hz, 1H; H$^7$), 7.5 (d, $^3$J(H,H)=8 Hz, 1H; H$^8$), 7.6 (d, $^3$J(H,H)=7.8 Hz, 1H; H$^5$), 7.7-7.8 (m, 4H; H$^3$H$^{21}$ and H$^{26}$), 7.9 (t, $^3$J(H,H)=7 Hz, 1H; H$^{20}$), 8.0 (d, $^3$J(H,H)=8 Hz, 1H; H$^{19}$), 8.1 (d, $^3$J(H,H)=8 Hz, 1H; H$^{22}$), 8.2 (s, 2H; H$^{10}$ and H$^{12}$), 8.42 (s, 1H; H$^{14}$), 9.04 (s, 1H; H$^{24}$), 9.29 (s, 1H; H$^{17}$); $^{19}$F NMR (376 MHz, d$_7$-DMF, 25° C.): δ −110.13 (t, $^3$J(F,H)=8 Hz); MS (+FAB): m/z: 674 [M$^+$]; elemental analysis calcd (%) for C$_{30}$H$_{17}$F$_2$ClN$_2$Pt (674.0): C, 53.46; H, 2.54; N, 4.16. found: C, 53.14, H, 2.42, N, 4.47.

Example 6

Example 6 describes the synthesis of Ligand 6 and Complex 6:

(a) The Synthesis Method and Physical Characterizations of Ligand 6:

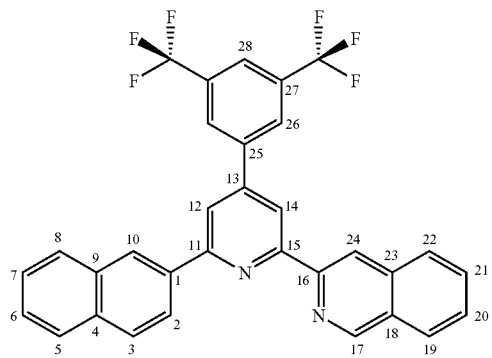

Ligand 6

3-acetylisoqulinoline was prepared from 3-hydroxyisoqulinoline using a Heck reaction (J. Y. Legros et al., *Tetrahedron* 57: 2507 (2001)). 1-(2-oxo-2-(3'-isoquinolinyl)ethyl) pyridinium iodide was prepared by heating 3-acetylisoqulinoline with excess 12 in pyridine for 2 hours (R. G. Pearson, *J. Am. Chem. Soc.* 69, 3100 (1947); L. C. King et al., *J. Am. Chem. Soc.* 70, 239 (1948)). α,β-unsaturated ketone (3',5'-bis(trifluoromethyl)benzylidene-2-acetonaphthone) were prepared according to the approach described in G. W. V. Cave et al., *J. Chem. Soc., Perkin Trans.* 1, 3258 (2001); F. Neve et al., *Inorg. Chem.* 36, 6150 (1997), for example.

Heating 1-(2-oxo-2-(3'-isoquinolinyl)ethyl)pyridinium iodide (0.95 g, 2.5 mmol), 3',5'-bis(trifluoromethyl)benzylidene-2-acetonaphthone (1.00 g, 2.54 mmol) and ammonium acetate (5.00 g, 64.9 mmol) in methanol (100 mL) for 24 hours gave crude Ligand 6. The crude product was filtered from the solution mixture, washed with water and cold methanol, and purified by column chromatography (silica gel, n-hexane/CHCl$_3$=9:1 as eluent) to afford Ligand 6 as off-white solid. Yield: 1.2 g, 85%.

$^1$H NMR (400 MHz, CDCl$_3$, 25° C., TMS): δ 7.5-7.6 (m, 2H; H$^6$ and H$^8$), 7.7 (t, $^3$J(H,H)=9 Hz, 1H; H$^{21}$), 7.8 (t, $^3$J(H,H)=8 Hz, 1H; H$^{20}$), 7.9-8.0 (m, 1H; H$^5$), 8.0-8.1 (m, 6H; H$^3$, H$^7$, H$^{12}$, H$^{19}$ and H$^{22}$), 8.3 (s, 2H; H$^{26}$), 8.4 (d, $^3$J (H,H)=10 Hz, 1H; H$^2$), 8.7 (s, 1H; H$^{10}$), 8.8 (s, 1H; H$^{14}$), 9.1 (s, 1H; H$^{24}$), 9.4 (s, 1H; H$^{17}$). $^{19}$F NMR (376 MHz, 25° C., TMS): δ −62.6; MS (70 eV, EI): m/z: 544 [M$^+$].

(b) The Synthesis Method and Physical Characterizations of Complex 6:

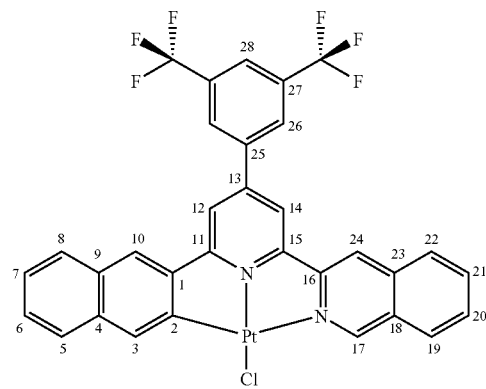

Complex 6

A mixture of $K_2PtCl_4$ (0.66 g, 1.6 mmol) and Complex 6 (0.86 g, 1.6 mmol) in glacial acetic acid (100 mL) was refluxed for 24 hours affording crude Complex 6 in a yellow suspension. The yellow solid was washed with water and acetone, and recrystallized in DMF. Complex 6 was isolated as a yellow crystalline solid. Yield: 1.1 g, 92%.

Complex 6: $^1$H NMR data were not available because the low solubility of Complex 6 in various deuterated solvents. $^{19}$F NMR (376 MHz, $d_7$-DMF, 25° C.): δ −62.1; MS (+FAB): m/z: 774 [M$^+$]; elemental analysis calcd (%) for $C_{32}H_{17}F_6ClN_2Pt$ (774.0): C, 49.66; H, 2.21; and N, 3.62. found: C, 49.67; H, 2.01; and N, 3.72.

Example 7

Example 7 shows the physical properties of non-limiting illustrative Complexes 1-6. The absorption and photoluminescent properties of Complexes 1-6 are provided in Table 1.

Figure 6:
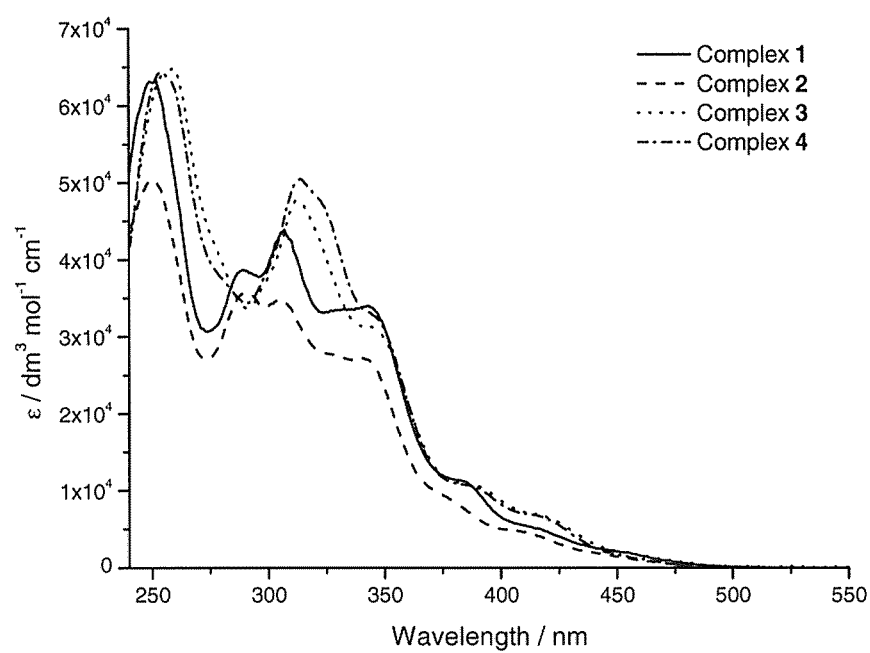
FIG. 6 is a plot of a UV-visible spectrum for embodiments of complexes, here complexes 1-4 in $CH_2Cl_2$ solution.
Figure 7:
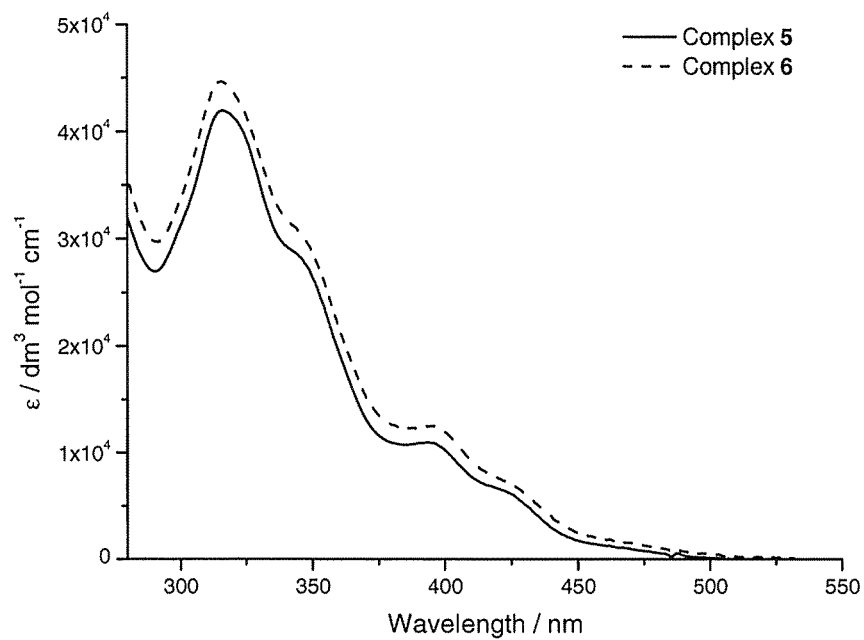
FIG. 7 is a plot of a UV-visible spectrum for embodiments of complexes, here complexes 5-6 in DMF solution.

The absorption spectra of Complexes 1-6 reveal several intense transitions at $\lambda_{max}$ ranging from 250-390 nm, which could be attributed to intraligand transitions since similar absorptions have been found in the free ligand. The broad absorption at 400-470 nm (ε≈6800-10000 $dm^3$ $mol^{-1}$ $cm^{-1}$) for Complexes 1-6 could be attributed to $^1$MLCT (5d)Pt→π* (L) transition, although mixing with IL is not necessarily excluded. The absorption tail at ~500 nm is tentatively attributed to $^3$MLCT transition. FIG. 6 and FIG. 7 show the UV-visible spectra of Complexes 1-4 in $CH_2Cl_2$ solution and Complexes 5-6 in DMF solution respectively.

Figure 8:
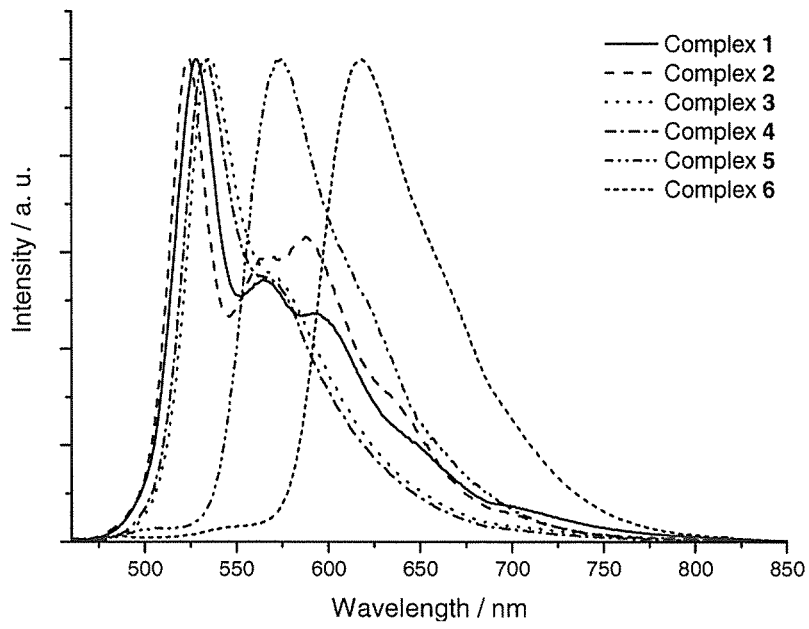
FIG. 8 is a plot of photo-luminescent spectra for embodiments of complexes, here complexes 1-6 in $CH_2Cl_2$ and DMF solution.

Complexes 1-6 are strongly emissive, with emission $\lambda_{max}$ affected by the substituent group R. The emission energy in solution follows the order of: R=3,5-($^t$Bu)$_2$Ph (Complexes 4, $\lambda_{max}$ at 533 nm)>phenyl (Complexes 3, 537 nm) in $CH_2Cl_2$ ($2\times10^{-5}$ M), and 3,5-$F_2$Ph (Complexes 5, 614 nm)>3,5-$(CF_3)_2$Ph (Complexes 6, 618 nm) in DMF ($2\times10^{-5}$ M). In the cases of Complexes 1-6, their emission spectra recorded in DMF solutions are not vibronically resolved. The emission of Complexes 1-6 at 525-618 nm ($CH_2Cl_2$, MeCN or DMF solutions) are attributed to have come from a triplet excited state with $^3$IL and $^3$MLCT parentage. There is a lack of dependence of the emission energies on the complex concentrations from $10^{-4}$ to $10^{-6}$ mol $dm^{-3}$, suggesting that the emissions are not excimeric $^3\pi$-$\pi$* or $^3$MMLCT in nature; these emissions are attributed to $^3$IL charge-transfer in nature. FIG. 8 shows the photo-luminescent spectra of Complexes 1-6 in $CH_2Cl_2$ and DMF solution.

The emission quantum yields of Complexes 1-6 in $CH_2Cl_2$ solutions range from 0.20 to 0.68, which are significantly higher than that of the congener [(C^N^N)PtCl] complexes ((C^N^N)=6-phenyl-2,2'-bipyridyl and derivatives, Φ≈0.03-0.07). It is likely that the extended π-conjugated (RC^N^N) ligands have a rigid structure, which disfavors deactivation of the excited state by non-radiative process(es). The emission quantum yields of Complexes 1-6 in DMF are 0.02-0.03, which are lower than that of Complexes 1-6 in $CH_2Cl_2$ solution, probably due to the quenching effect by DMF.

Figure 9:
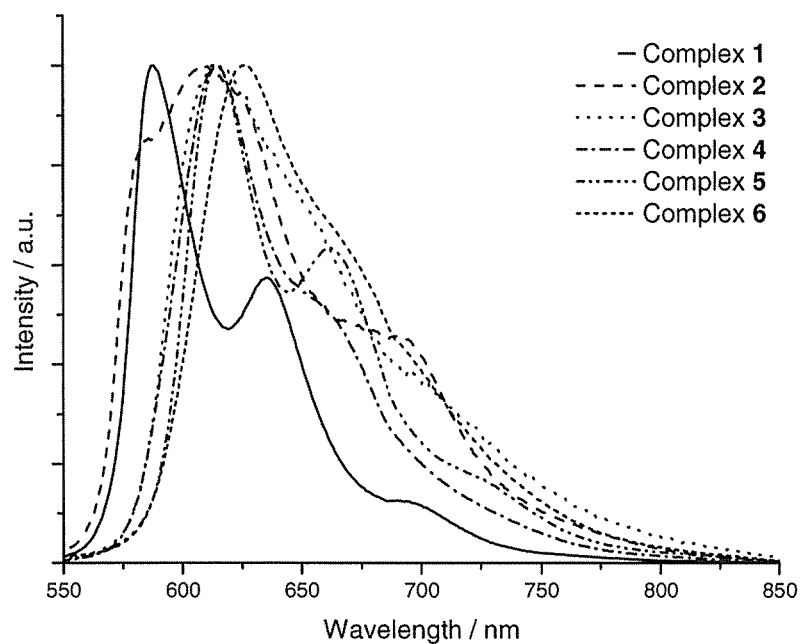
FIG. 9 is a plot of solid-state photo-luminescent spectra for embodiments of complexes, here complexes 1-6 at 298 K.

In solid state at room temperature, Complexes 1-6 show a vibronic structured emission with $\lambda_{max}$ at 588-633 nm. Upon cooling to 77 K, the emission slightly blue shifts. These emissions are attributed to come from $^3$MLCT excited states. Glassy solutions (2-MeTHF or DMF/MeOH/EtOH, 1:1:4, $4\times10^{-5}$ M) of Complexes 1-6 were found to exhibit similar vibronically structured emission with peak maxima at 518-537 nm. The spacings are 1300-1400 $cm^{-1}$, which correspond to skeletal vibrational frequencies of C=C/C=N entities of the (RC^N^N) ligands. FIG. 9 shows the solid-state photo-luminescent spectra of Complexes 1-6 at 298 K.

Figure 10:
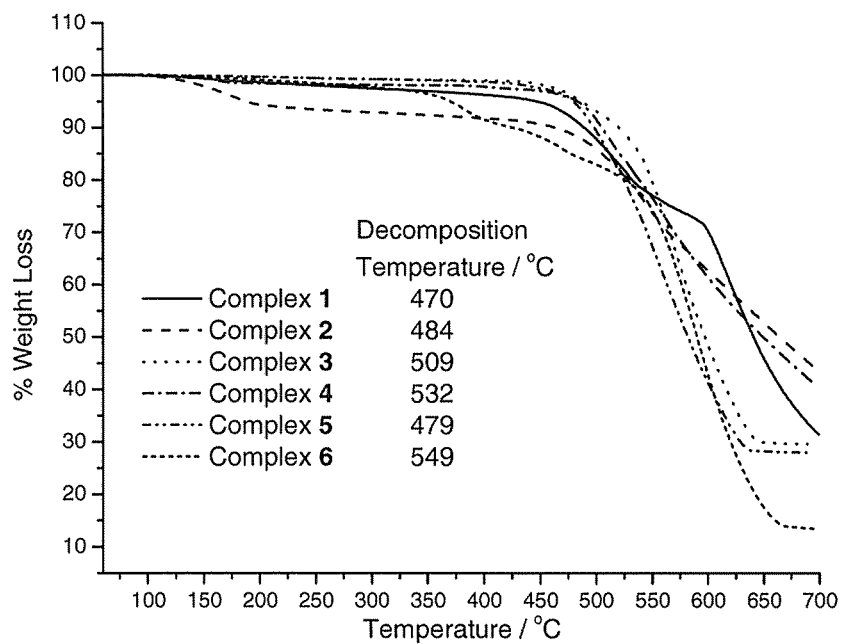
FIG. 10 is a plot of thermo-grams for example embodiments of complexes, here complexes 1-6.

The thermal behavior of the illustrative materials was measured using thermogravimetric analyses (TGA) at heating rate of 20° C. $min^{-1}$. TGA measures weight changes in a material as a function of temperature (or time) under a controlled atmosphere. Complexes 1-6 possess relatively high thermal stability and are stable to air and moisture; their decomposition temperature ($T_d$) ranges from 470 to 549° C. as shown in FIG. 10 and Table 1.

TABLE 1

Physical properties of illustrative Complexes 1-6.

| Complexes | Medium (T/K) | $\lambda_{abs}$/nm$^{a,b}$ (ε/× $10^4$ $dm^3$ $mol^{-1}$ $cm^{-1}$) | $\lambda_{em}$/nm$^c$ (τ/μs); $k_q$/$10^9$s$^{-1}$dm$^{-1}$mol$^{-1}$ $^g$ | $\Phi_{em}^d$ | $T_d$/° C.$^f$ |
|---|---|---|---|---|---|
| 1 | $CH_2Cl_2$ (298) | 249 (6.29), 289 (3.84), 307 (4.36), 343 (3.37), 381 (1.12), 416 (0.48), 451 (0.18), 500 (~0.01) | 529 (6), 566, 595$^e$; 6.8 | 0.20 | 470 |
|   | Solid (298) | — | 588 (6), 635 (6), 694 (6) | — |   |
|   | Solid (77) | — | 588 (14), 639 (14), 699 (14) | — |   |
|   | 2-MeTHF (77) | — | 521 (88), 563 (88), 609 (88)$^b$ | — |   |
| 2 | $CH_2Cl_2$ (298) | 250 (5.01), 290 (3.54), 305 (3.46), 342 (2.68), 375 (0.92), 408 (0.44), 450 (0.11), 500 (~0.01) | 525 (6), 566, 591 (6), 633, 703$^e$; 0.8 | 0.29 | 484 |
|   | Solid (298) | — | 609 (1), 693 (1) | — |   |
|   | Solid (77) | — | 578 (13), 593 (13), 626 (13) | — |   |
|   | 2-MeTHF (77) | — | 518 (97), 567 (97), 576 (32), 624 (32)$^b$ | — |   |
| 3 | $CH_2Cl_2$ (298) | 260 (6.40), 313 (4.69), 344 (3.04), 387 (0.99), 417 (0.60), 454 (0.10), 500 (~0.02) | 537 (7), 570$^e$; 9.0 | 0.42 | 509 |
|   | Solid (298) | — | 615 (5) | — |   |
|   | Solid (77) | — | 603 (9), 654 (9) | — |   |
|   | 2-MeTHF (77) | — | 525 (43), 567 (43), 614 (43)$^b$ | — |   |
| 4 | $CH_2Cl_2$ (298) | 254 (6.43), 314 (5.05), 344 (3.30), 386 (1.07), 415 (0.68), 458 (0.12), 500 (~0.01) | 533 (7), 569$^e$; 1.6 | 0.68 | 532 |
|   | DMF (298) | 351 (4.84), 324 (4.89), 386 (1.22), 416 (0.78), 450 (0.22) | 601 (11)$^e$; 0.5 | 0.02 |   |
|   | Solid (298) | — | 613 (2), 659 (2) | — |   |
|   | Solid (77) | — | 610 (11), 659 (11), 720 (11) | — |   |
|   | 2-MeTHF (77) | — | 523 (52), 566 (52), 617 (52)$^b$ | — |   |
| 5 | DMF (298) | 315 (4.19), 343 (2.88), 395 (1.09), 422 (0.64), 465 (0.11), 500 (~0.01) | 614 (0.7)$^e$; 1.2 | 0.03 | 479 |

TABLE 1-continued

Physical properties of illustrative Complexes 1-6.

| Complexes | Medium (T/K) | $\lambda_{abs}$/nm$^{a,b}$ ($\epsilon$/× 10$^4$ dm$^3$ mol$^{-1}$ cm$^{-1}$) | $\lambda_{em}$/nm$^c$ ($\tau$/μs); $k_q$/10$^9$s$^{-1}$dm$^{-1}$mol$^{-1}$ $^g$ | $\Phi_{em}$$^d$ | $T_d$/° C.$^f$ |
|---|---|---|---|---|---|
| | Solid (298) | — | 615 (3), 661 (3), 725 (3) | — | |
| | Solid (77) | — | 615 (10), 668 (10), 728 (10) | — | |
| | 2-MeTHF (77) | — | 532 (33), 575 (33), 619 (33)$^b$ | — | |
| 6 | DMF (298) | 316 (4.41), 344 (3.03), 395 (1.19), 427 (0.61), 467 (0.10), 500 (~0.04) | 618 (0.7)$^e$; 0.9 | 0.02 | 549 |
| | Solid (298) | — | 626 (2) | — | |
| | Solid (77) | — | 618 (12), 669 (12) | — | |
| | DMF/MeOH/ EtOH, 1:1:4 (77) | — | 537 (35), 596 (35), 650 (35), 715 (35)$^b$ | — | |

$^a$Absorption maxima.
$^b$at 4 × 10$^{-5}$ M.
$^c$Emission maxima.
$^d$Emission quantum yield.
$^e$at 2 × 10$^{-5}$ M.
$^f$Decomposition Temperature.

Example 8

Example 8 illustrates a non-limiting method embodiment for preparing OLED A. The OLED was prepared on patterned indium-tin-oxide (ITO) glass with a sheet resistance of 20Ω/☐. Thermal vacuum deposition of the materials was carried out sequentially under a vacuum of 1×10$^{-6}$ torr in a thin film deposition system (e.g., a MBraun three-glove boxes system integrated with an Edwards Auto 306 and spin coater instrument). The devices were encapsulated using anodized aluminum caps and their performance was examined using Photoresearch PR-650. The current-voltage characteristics were studied using a Keithley 2400 sourcemeter.

Figure 11:
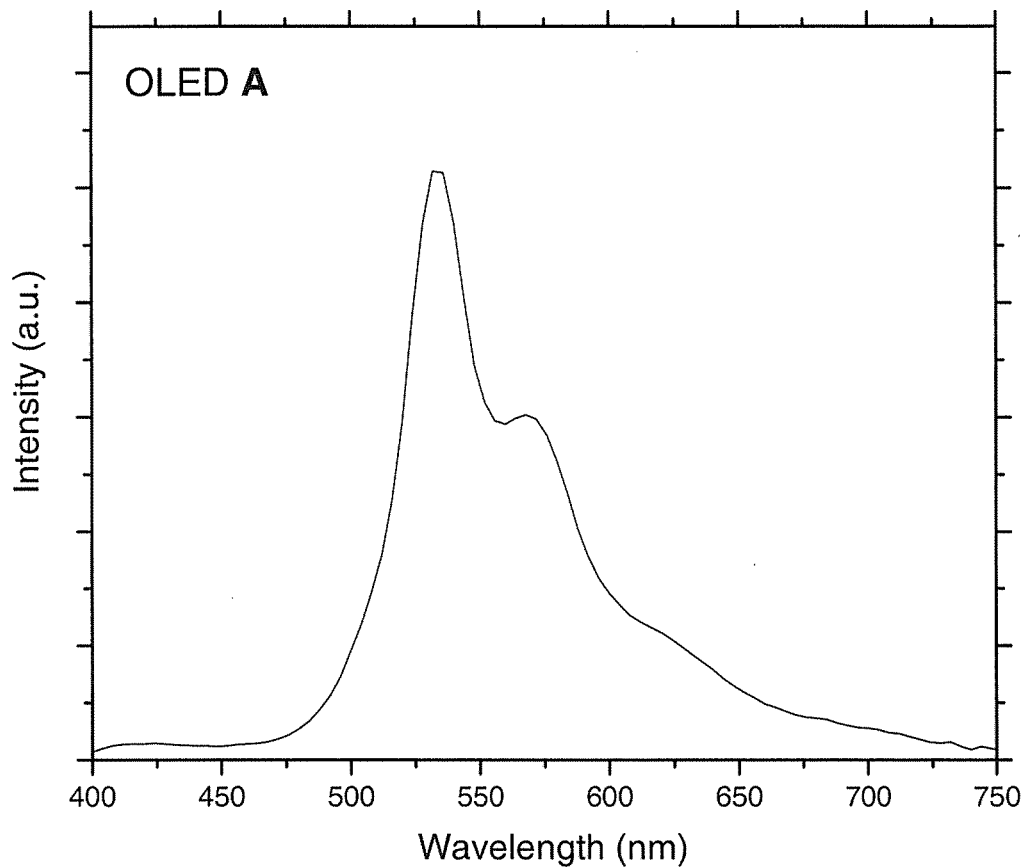
FIG. 11 is a plot of an EL spectrum for OLED A.
Figure 12:
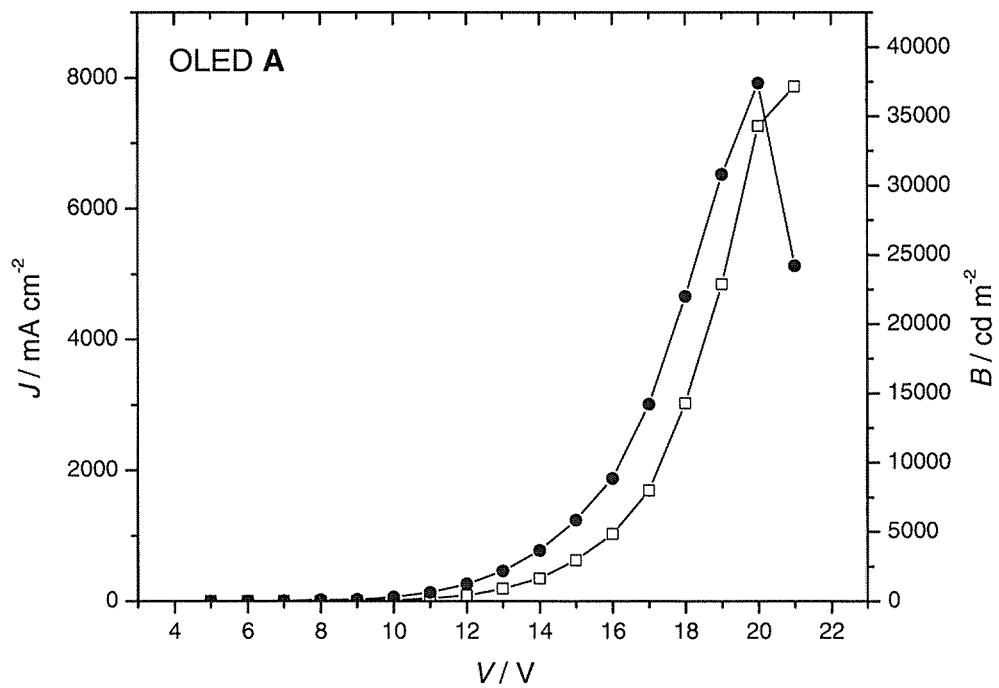
FIG. 12 is a plot of J-V-B relationships for OLED A.
Figure 13:
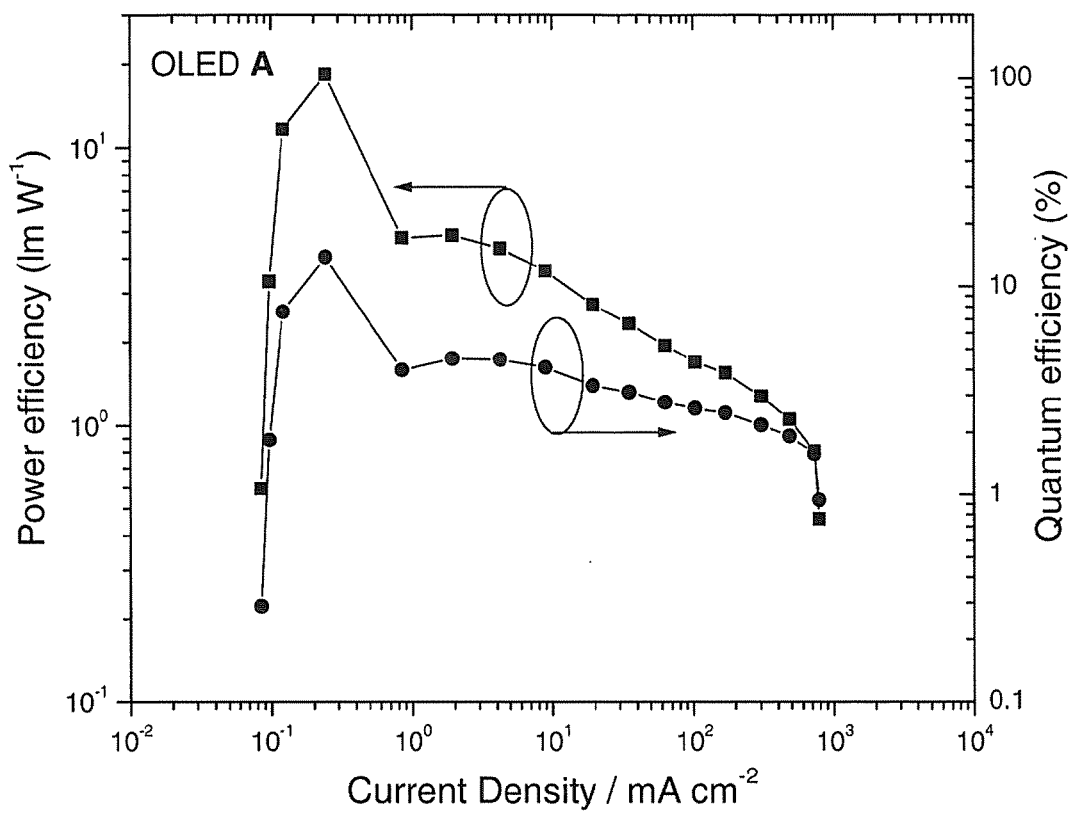
FIG. 13 is a plot of external quantum efficiency-current density and power efficiency-current density relationships for OLED A.

OLED A employing Complex 1 has the following configuration: ITO (indium tin oxide)/NPB (4,4'-bis[N-(1-naphthyl)-N-phenylamino]biphenyl, 70 nm)/CBP (4,4'-N,N-dicarbazolebiphenyl): Complex 1, 5%, 30 nm)/BCP (bathocuprine, 15 nm)/Alq$_3$ (tris(8-quinolinolato)aluminum, 30 nm)/LiF (0.3 nm)/Al (130 nm). OLED A was observed to emit yellow-green light (CIE=0.37, 0.58); strong emission was observed with peak maxima at 532 and 570 nm with a shoulder at ~610 nm, which could be attributed to come from the triplet excited state of Complex 1. A brightness of 1 cd m$^{-2}$ was obtained at 5 V. The maximum brightness of 37400 cd m$^{-2}$ was achieved at 20 V. The peak external quantum efficiency, luminous and power efficiencies are 14%, 46 cd A$^{-1}$, and 18 lm W$^{-1}$ at 0.24 mA cm$^{-2}$, respectively, corresponding to a brightness of 114 cd m$^{-2}$. The EL spectrum of OLED A, the J-V-B (Current density-voltage-brightness) relationships of OLED A and the graph of external quantum efficiency and power efficiency of the OLED A as a function of drive current density are shown in FIG. 11, FIG. 12 and FIG. 13, respectively.

Example 9

Figure 14:
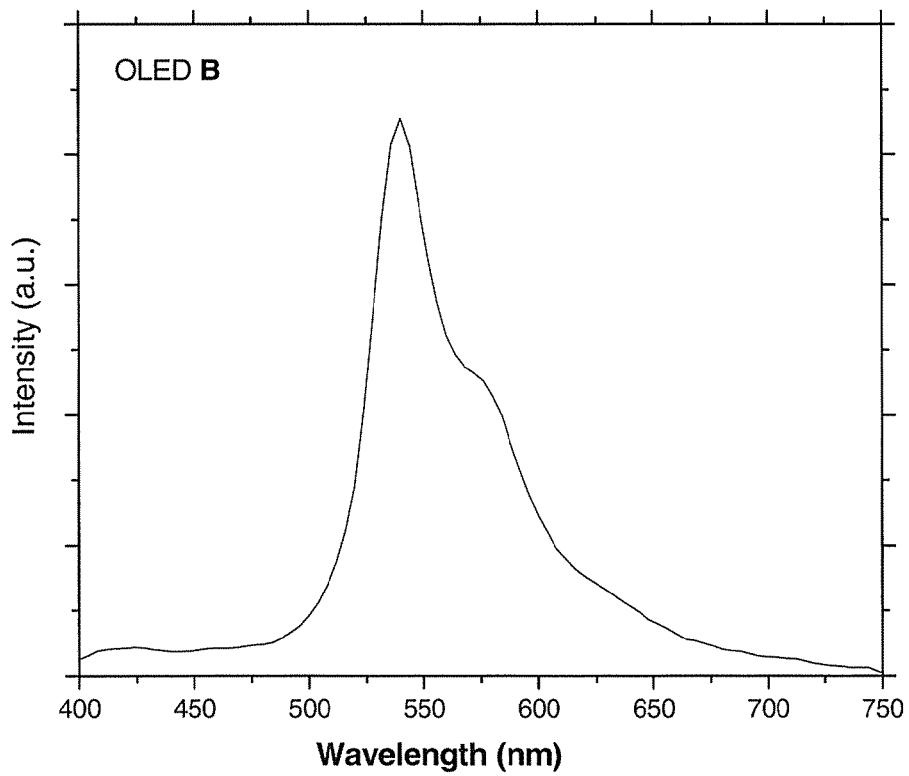
FIG. 14 is a plot of an EL spectrum for OLED B.
Figure 15:
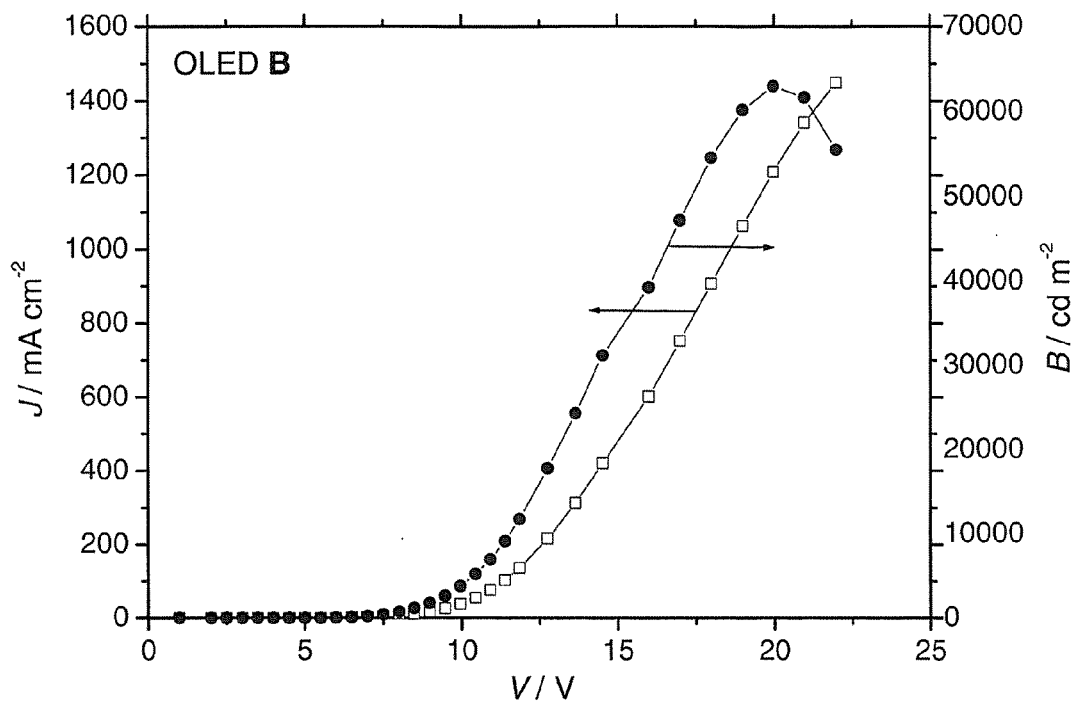
FIG. 15 is a plot of J-V-B relationships for OLED B.
Figure 16:
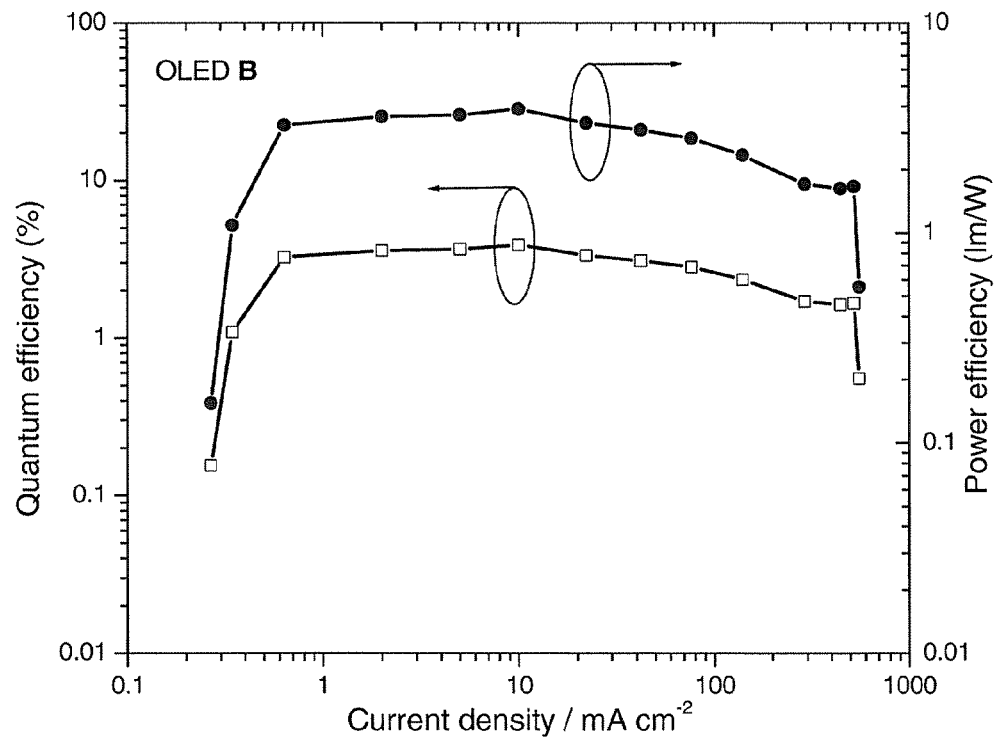
FIG. 16 is a plot of external quantum efficiency-current density and power efficiency-current density relationships for OLED B.
Figure 17:
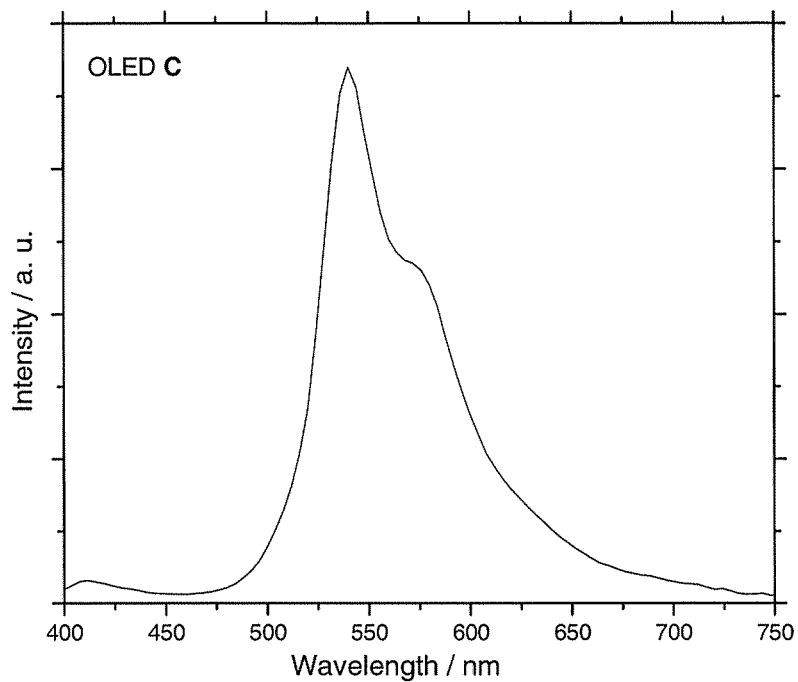
FIG. 17 is a plot of an EL spectrum for OLED C.
Figure 18:
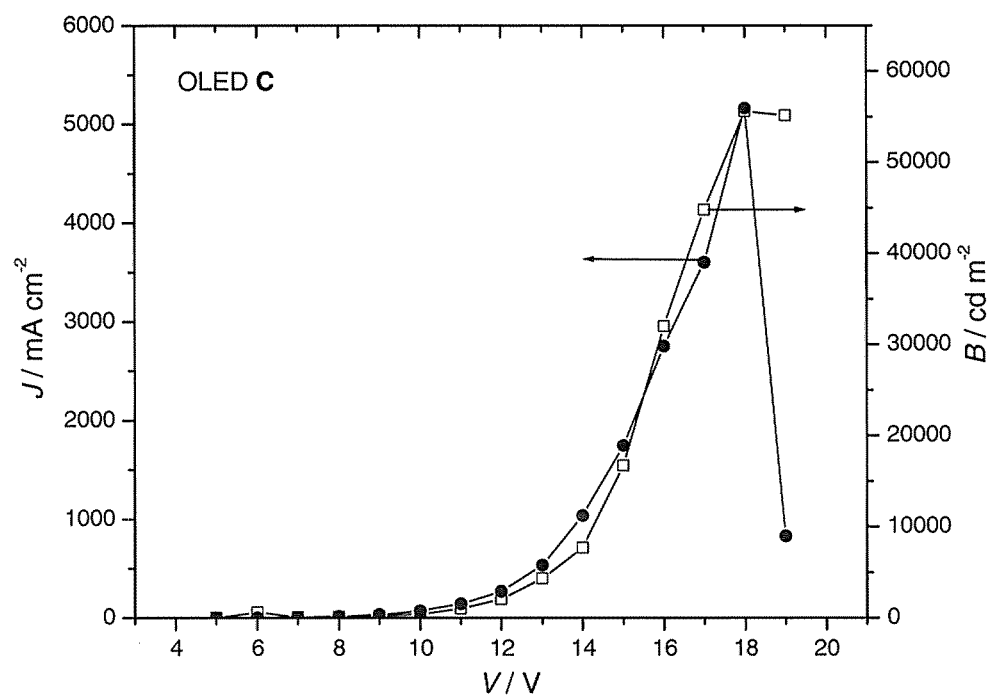
FIG. 18 is a plot of J-V-B relationships for OLED C.
Figure 19:
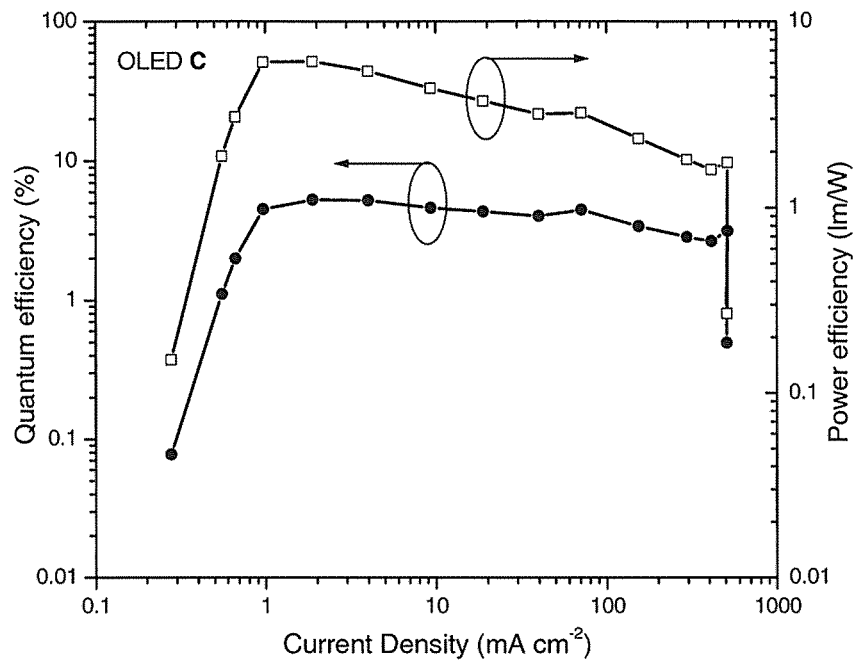
FIG. 19 is a plot of external quantum efficiency-current density and power efficiency-current density relationships for OLED C.

Example 9 illustrates a non-limiting method embodiment for preparing OLED B and C. The OLEDs were prepared on patterned indium-tin-oxide (ITO) glass with a sheet resistance of 20Ω/☐C. Thermal vacuum deposition of the materials was carried out sequentially under a vacuum of 1×10$^{-6}$ torr in a thin film deposition system (e.g., a MBraun three-glove boxes system integrated with an Edwards Auto 306 and spin coater instrument). The devices were encapsulated using anodized aluminum caps and their performance was examined using Photoresearch PR-650. The current-voltage characteristics were studied using a Keithley 2400 sourcemeter. OLED B and OLED C employing Complex 4 have the following configuration: ITO (indium tin oxide)/NPB (4,4'-bis [N-(1-naphthyl)-N-phenylamino]biphenyl, 40 nm)/CBP (4,4'-N,N-dicarbazolebiphenyl): Complex 4, X %, 30 nm)/BAlq$_3$ (Bis(2-methyl-8-quinolinolato)(4-phenylphenolato) aluminum, 10 nm)/Alq$_3$ (30 nm)/LiF (0.1 nm)/Al (200 nm). OLED B (X=1%) and OLED C (X=3%) offered the highest maximum brightness and the current efficiency, respectively. These devices were observed to emit yellowish green light with similar CIE coordinates (CIE=0.36, 0.54 for OLED B; CIE=0.38, 0.55 for OLED C). The EL $\lambda_{max}$(540, 592 nm with a shoulder at 640 nm) is independent of the doping concentrations for Complex 4. The turn-on voltage of OLED B was 5 V at a brightness of 1 cd m$^{-2}$, and a maximum current efficiency of 12.5 cd A$^{-1}$ was obtained at 1.8 mA cm$^{-2}$. A maximum brightness was 63000 cd m$^{-2}$ at 20 V. FIG. 14, FIG. 15 and FIG. 16 show the EL spectrum, the J-V-B curves, and the external quantum efficiency and power efficiency as a function of drive current density for OLED B, respectively. Also, the EL spectrum, the J-V-B curves, and the external quantum efficiency and power efficiency as a function of drive current density of OLED C are shown in FIG. 17, FIG. 18 and FIG. 19, respectively.

Example 10

Example 10 illustrates a method for preparing WOLED A. The organic layers were deposited by high-vacuum (10$^{-6}$ Torr) thermal evaporation onto a cleaned glass substrate pre-coated with transparent, conductive indium tin oxide (ITO) in a thin film deposition system (e.g., a MBraun three-glove boxes system integrated with an Edwards Auto 306 and spin coater instrument). A 30 nm-thick film of NPB (4,4'-bis[N-(1-naphthyl)-N-phenylamino]biphenyl) served as the hole-transporting layer (HTL). A 10 nm-thick light-emitting layer (EML) comprising a CBP (4,4'-N,N'-dicarbazolebiphenyl) host was deposited while being doped with 5 wt.-% Complex 1. The doping level was controlled by the deposition rates. Introduction of such a thin layer is to reduce operational voltage. A 2 nm-thick layer of DNA (9,10-bis-(β-naphthyl)-anthrene) was used as a blue light emission layer and a 4 nm thick layer of BCP was used to confine excitons in the EML. A 30 nm-thick layer of tris-(8-hydroxy-quinoline)aluminum (Alq3) was used to transport and inject electrons into the EML. A shadow mask with a 3×3 mm² opening was used to define the cathode comprising a 0.3 nm-thick layer of LiF and a 130 nm-thick aluminum cap.

Figure 20:
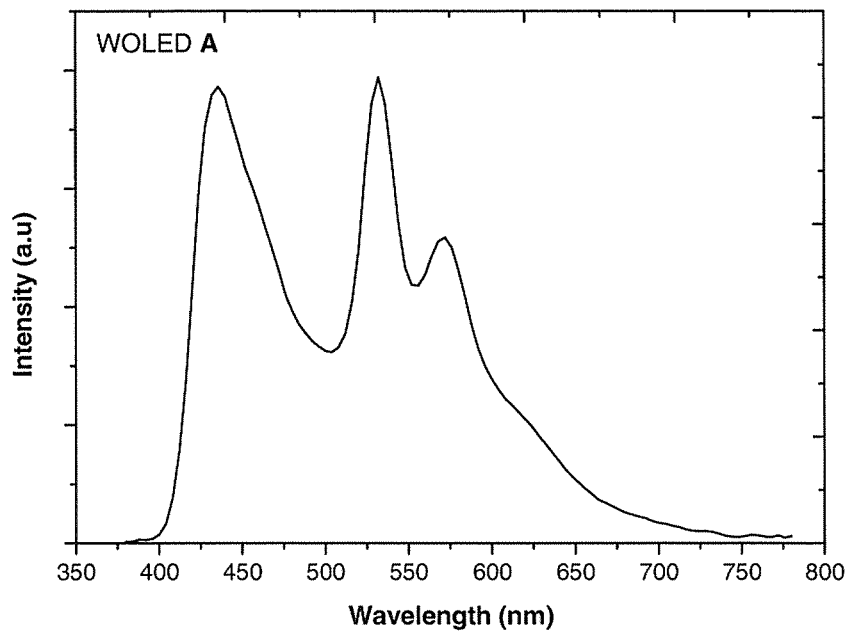
FIG. 20 is a plot of an EL spectrum for WOLED A.

The electroluminescent (EL) spectra, brightness and Commission Internationale de L'Eclairage coordinates (CIE) of OLEDs were measured with a Photo Research Inc. PR650 luminance meter. The luminance-current density-voltage characteristics were recorded with the measurement of the EL spectra by combining the luminance meter and with a Keithley model 2400 voltage-current source. Measurements were carried out at room temperature under ambient conditions. The EL spectrum of the white light-emitting device was influenced by the thickness of the yellow-green emissive layer and doping concentration of Complex 1. The doping concentration for the Pt(II) phosphorescent material was determined from the efficiency of single emissive layer OLED A in example 10. The maximum external quantum efficiency is 14% for 5% doping concentration. FIG. 20 shows the EL spectrum of WOLED A. It revealed that EL spectrum covers the wavelength region of visible light spectrum, from 400 to 700 nm. The spectrum contains three peaks at maxima 436, 532 and 570 nm. The emission at 450 nm is from DNA. The strong emission at 532 and 570 nm is from the triplet excited states, which are all from Complex 1. If the applied voltage was increased from 7.5 to 15.5 V, CIE coordinates changed from (0.26, 0.31) to (0.33, 0.39), within the white light region.

Figure 21:
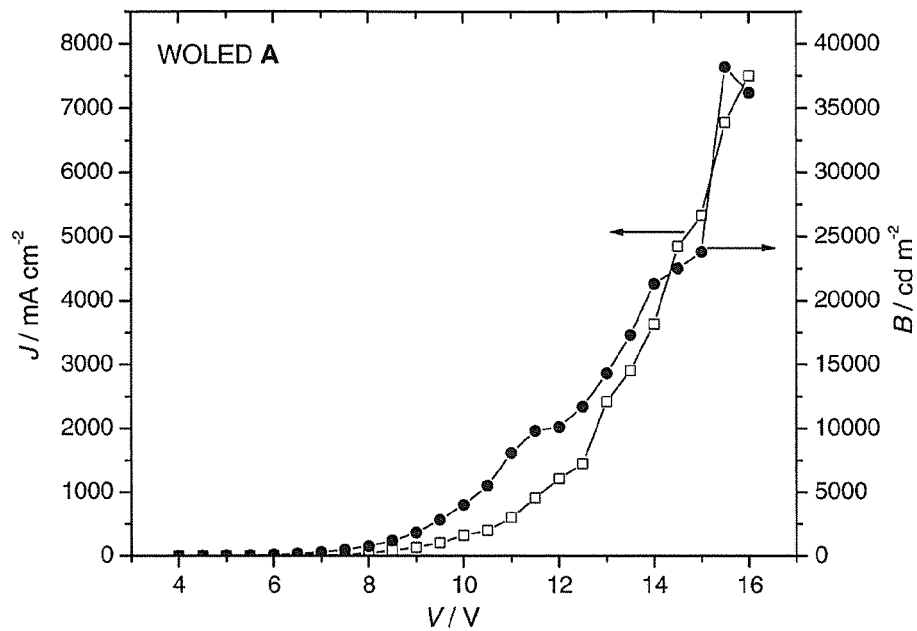
FIG. 21 is a plot of J-V-B relationships for WOLED A.

FIG. 21 shows the J-V-B curves of WOLED A with 5 wt.-% Complex 1. The threshold voltage of WOLED A is <4 V for 1 cd/m². At a luminance of 1000 cd/m², the applied voltage is 8.5 V, and at a luminance of 10000 cd/m², the voltage is 11.5 V. WOLED A exhibits the maximum luminance of 38200 cd/m² at a current density of 622 mA/cm² (at 15.5 V).

Figure 22:
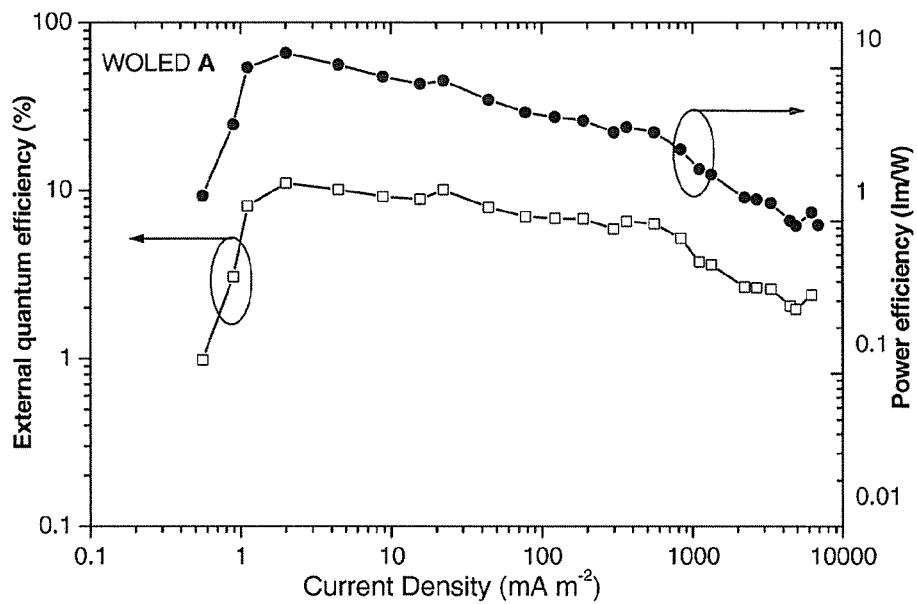
FIG. 22 is a plot of external quantum efficiency-current density and power efficiency-current density relationships for WOLED A.

The external quantum efficiency and power efficiency of WOLED A as a function of drive current density are shown in FIG. 22. The peak external quantum efficiency ($\eta_{ext}$) and power efficiency ($\eta_p$) are 11% and 13 lm/W, respectively, corresponding to a drive current density of 0.2 mA/cm² (5.5 V). At the benchmark brightness of 100 cd/m², the external quantum efficiency and power efficiency are 10.1% and 10.6 lm/W, respectively, corresponding to a drive current density of 0.44 mA/cm² (6 V). At a luminance of 1000 cd/m², the external quantum efficiency and power efficiency are 7.3% and 6.0 lm/W, respectively.

Example 11

Example 11 illustrates a method for preparing WOLED B. The organic layers were deposited by high-vacuum ($10^{-6}$ Torr) thermal evaporation onto a cleaned glass substrate pre-coated with transparent, conductive indium tin oxide (ITO) in a thin film deposition system (e.g., a MBraun three-glove boxes system integrated with an Edwards Auto 306 and spin coater instrument). A 30 nm-thick film of NPB (4,4'-bis[N-(1-naphthyl)-N-phenylamino]biphenyl) served as the hole-transporting layer (HTL). A 10 nm-thick light-emitting layer (EML) comprising a CBP (4,4'-N,N-dicarbazolebiphenyl) host was deposited while being doped with 6.3 wt.-% Complex 6. The doping level was controlled by the deposition rates. A 1 nm-thick layer of DNA (9,10-bis-(β-naphthyl)-anthracene) was used as a blue light emission layer and a 4 nm thick layer of BCP was used to confine excitons in the EML. A 30 nm-thick layer of tris-(8-hydroxy-quinoline)aluminum (Alq3) was used to transport and inject electrons into the EML. A shadow mask with a 3×3 mm² opening was used to define the cathode comprising a 0.5 nm-thick layer of LiF and 100 nm-thick aluminum cap.

Figure 23:
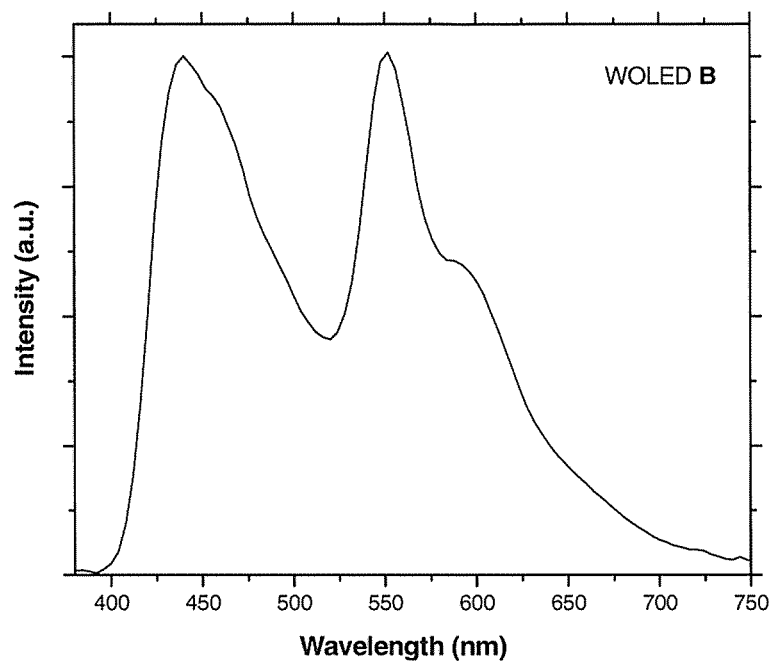
FIG. 23 is a plot of an EL spectrum for WOLED B.

The electroluminescent (EL) spectra, brightness and Commission Internationale de L'Eclairage coordinates (CIE) of OLEDs were measured with a Photo Research Inc. PR650 luminance meter. The luminance-current density-voltage characteristics were recorded with the measurement of the EL spectra by combining the luminance meter and with a Keithley model 2400 voltage-current source. Measurements were carried out at room temperature under ambient conditions. The maximum external quantum efficiency is 4.01% for 6.3% doping concentration. FIG. 23 shows the EL spectrum of WOLED B. It revealed that EL spectrum covers the wavelength region of visible light spectrum, from 400 to 700 nm. The spectrum contains three peaks at maxima 440, 552 and 592 nm. The emission at 440 nm is from DNA. The strong emission at 552 and 592 nm is from the triplet excited states of Complex 6. If the applied voltage was increased from 7.5 to 13.5 V, CIE coordinates changed from (0.29, 0.31) to (0.32, 0.35), within the white light region.

Figure 24:
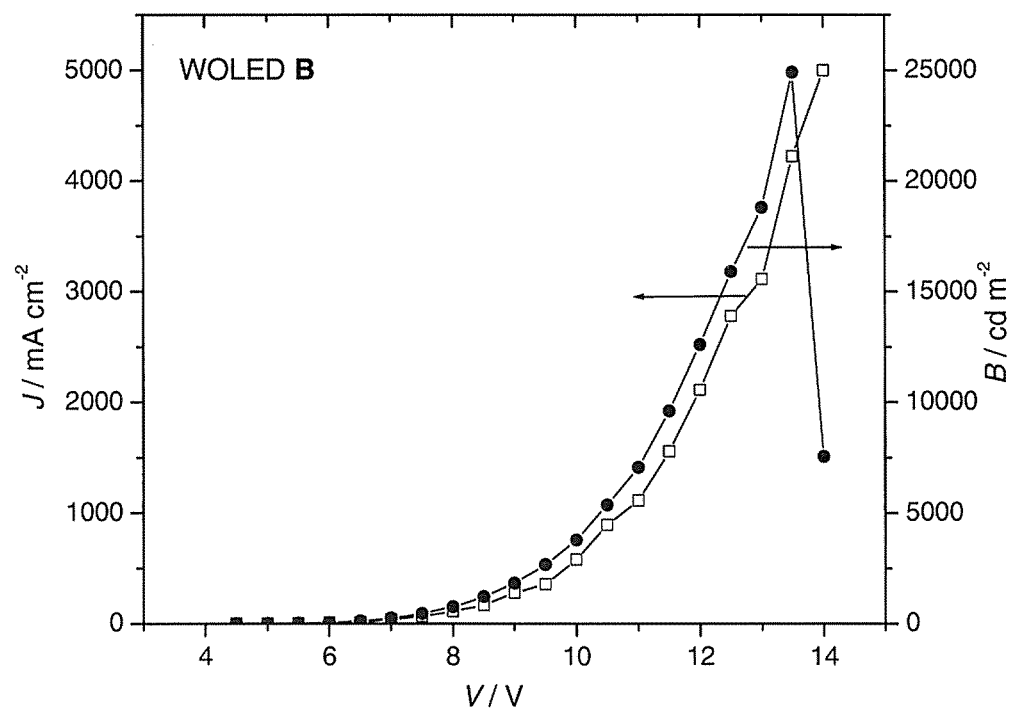
FIG. 24 is a plot of J-V-B relationships for WOLED B.

FIG. 24 shows J-V-B curves of WOLED B with 6.3 wt.-% Complex 6. The threshold voltage of WOLED B is <5 V for 1 cd/m². At a luminance of 1210 cd m⁻², the applied voltage is 8.5 V, and at a luminance of 12600 cd m⁻², the voltage is 12 V. WOLED B exhibits the maximum luminance of 24900 cd m⁻² at a current density of 422 mA cm⁻² (at 13.5 V) and a CRI of 73.

Figure 25:
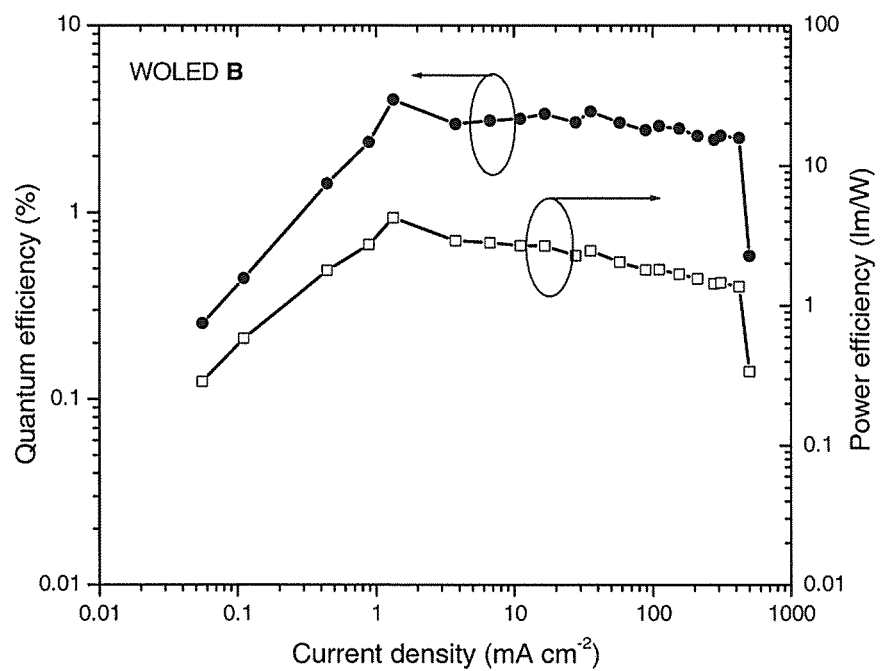
FIG. 25 is a plot of external quantum efficiency-current density and power efficiency-current density relationships for WOLED B.

The external quantum efficiency and power efficiency of the WOLED B as a function of drive current density are shown in FIG. 25. The peak external quantum efficiency ($\eta_{ext}$) and power efficiency ($\eta_p$) are 4.01% and 4.25 lm W⁻¹, respectively, corresponding to a drive current density of 1.3 mA cm⁻² (6.5 V). At a luminance of 1210 cd m⁻², the external quantum efficiency and power efficiency are 3.36% and 2.66 lm W⁻¹, respectively.

In the preceding description, various aspects of claimed subject matter have been described. For purposes of explanation, specific numbers, systems and/or configurations were set forth to provide a thorough understanding of claimed subject matter. However, it should be apparent to one skilled in the art having the benefit of this disclosure that claimed subject matter may be practiced beyond the specific details provided. In other instances, well-known features were omitted and/or simplified so as not to obscure claimed subject matter. While certain features have been illustrated and/or described herein, many modifications, substitutions, changes and/or equivalents will now occur to those skilled in the art. It is, therefore, to be understood that the appended claims are intended to cover all such modifications and/or changes as fall within the true spirit of claimed subject matter.

What is claimed is:

1. An organometallic complex used as a light-emitting material in an electroluminescent (EL) device, an organic light-emitting device (OLED), a polymer light-emitting device (PLED), a photovoltaic cell, a field-effect transistor, a sensor, or a laser comprising:
    an extended π-conjugated tridentate ligand having a platinum center, wherein the ligand comprises an extended π-conjugated tridentate ligand having the following structures:

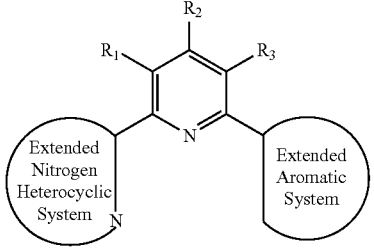

wherein $R_1$-$R_3$ are independently hydrogen, halogen, hydroxyl, an unsubstituted alkyl, a substituted alkyl, cycloalkyl, aryl, acyl, alkoxy, acyloxy, amino, acylamino, aralkyl, cyano, carboxyl, thio, styryl, aminocarbonyl, carbamoyl, aryloxycarbonyl, phenoxycarbonyl, or an alkoxycarbonyl group; $R_2$ and $R_5$ can also be substituted aryl group;

wherein if the $R_1$-$R_6$ substituents are not monovalent group(s), they can form a ring together with the group on which they are substituted;

wherein the extended nitrogen heterocyclic system independently has one of the following structures:

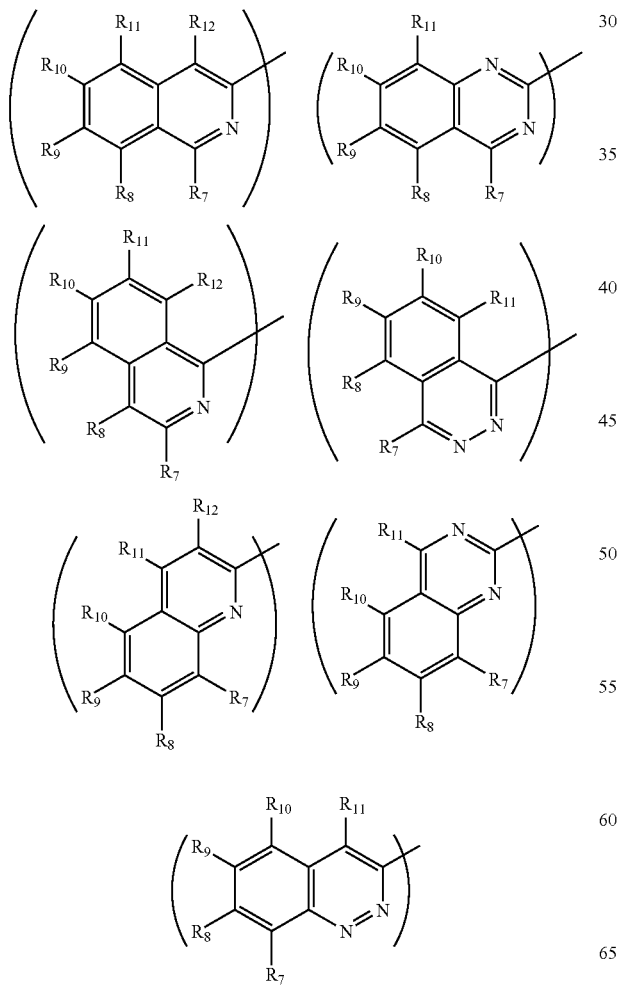

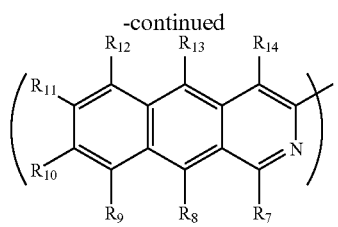

where $R_7$-$R_{14}$ are hydrogen, halogen, hydroxyl, unsubstituted alkyl, an substituted alkyl, cycloalkyl, an aryl, acyl, alkoxy, acyloxy, amino, acylamino, aralkyl, cyano, carboxyl, thio, styryl, aminocarbonyl, carbamoyl, aryloxycarbonyl, phenoxycarbonyl, or an alkoxycarbonyl group;

where if the $R_7$-$R_{14}$ substituents are not monovalent groups(s), they can form a ring together with the group on which they are substituted; and wherein the extended aromatic systems have one of the following structures:

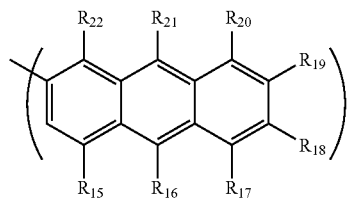

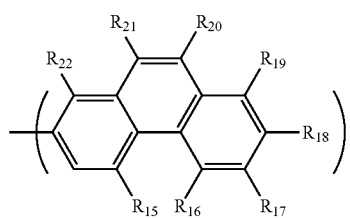

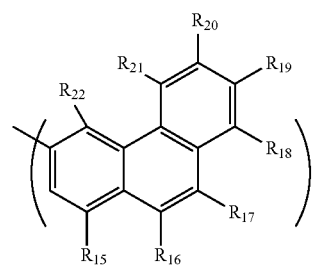

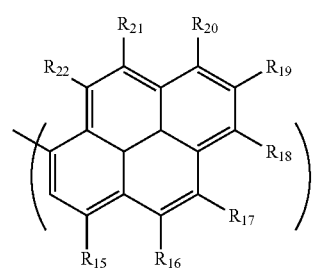

-continued

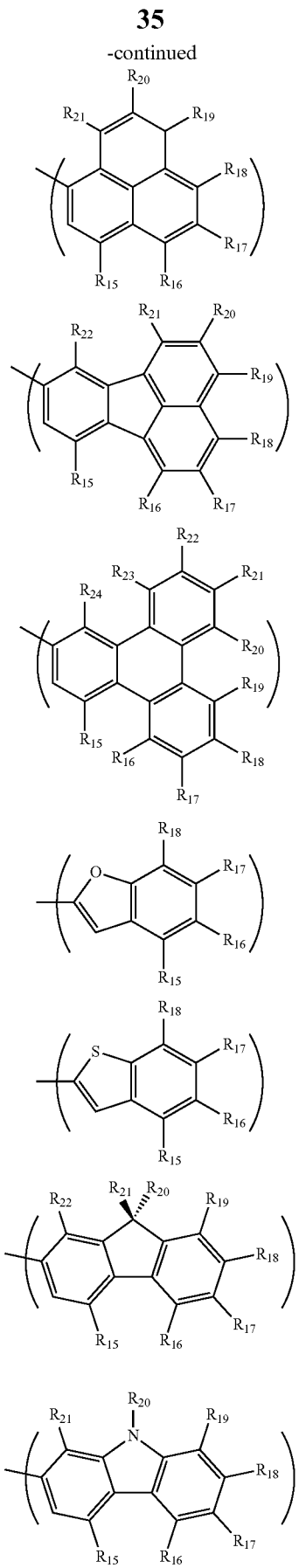

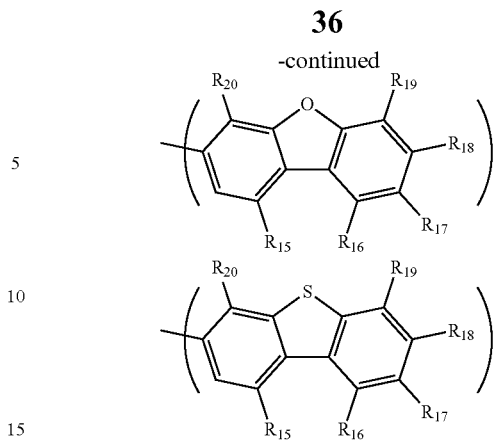

where $R_{15}$-$R_{22}$ are independently hydrogen, halogen, hydroxyl, unsubstituted alkyl, substituted alkyl, cycloalkyl, aryl, acyl, alkoxy, acyloxy, amino, acylamino, aralkyl, cyano, carboxyl, thio, styryl, aminocarbonyl, carbamoyl, aryloxycarbonyl, phenoxycarbonyl, or an alkoxycarbonyl group; and where if the $R_{15}$-$R_{22}$ are not monovalent group(s), they can form a ring together with the group on which they are substituted.

2. The organometallic complex of claim 1, wherein the extended π-conjugation tridentate ligand coordinates to the platinum center through two nitrogen bonds and a carbon bond, wherein the tridentate ligand bears a formal negative charge localized at a site of a metal-carbon bond, and wherein the extended π-conjugation tridentate ligand has the following chemical structure:

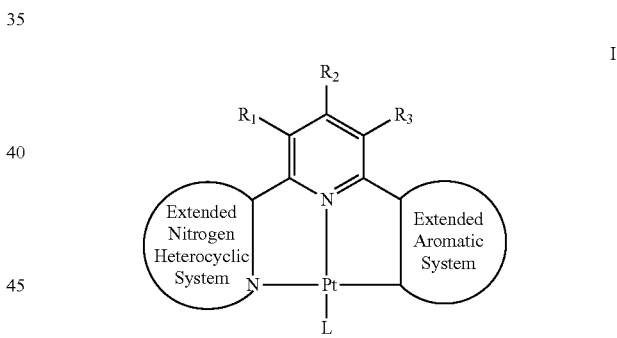

I wherein L comprises one of the following:
(1) a negatively charged of fluoride, chloride, bromide, or iodide atom;
(2) a ligand group capable of forming a carbon metal bond in the organometallic complex, including an acetylide, an alkenyl, an unsubstituted aryl, a substituted aryl, an unsubstituted alkyl, a substituted alkyl, a cyano, a cyclopentienyl, a vinyl, an allyl, or an alkyl group; or
(3) R'E, wherein E comprises a substituent that is capable of forming a bond to platinum includes an N, O, S, or Se wherein atom and R' is hydrogen, halogen, hydroxyl, unsubstituted alkyl, substituted alkyl, cycloalkyl, aryl, acyl, alkoxy, acyloxy, amino, acylamino, aralkyl, cyano, carboxyl, thio, styryl, aminocarbonyl, carbamoyl, aryloxycarbonyl, phenoxycarbonyl, or an alkoxycarbonyl group.

3. The organometallic complex of claim 1, wherein the complex is being deposited using thin layer vacuum deposition.

4. The organometallic complex of claim 1, wherein the light-emitting material is applied using spin-coating.

5. A heterostructure light-emitting device comprising:
a substrate;
a first electrode deposited over the substrate;
a first hole transporting layer;
a first emissive layer comprising a host material and an emitting/dopant complex, wherein the emitting/dopant complex is the organometallic complex of claim 1;
a hole blocking layer;
an electron transporting layer; and
a second electrode deposited over the electron transporting layer, sandwiching the hole transporting layer, emissive layer, hole blocking layer and electron transporting layer between the first and the second electrodes.

6. The heterostructure light-emitting device of claim 5, further comprising:
a second hole transporting layer;
a blue emissive layer;
wherein the second electrode sandwiches the hole transporting layer, the first emissive layer, the second hole transporting layer, the blue emissive layer, the hole blocking layer and the electron transporting layer between the first and the second electrodes.

7. The heterostructure light-emitting device of claim 5, wherein the hole transporting layer is naphthylphenylbiphenylamine (NPB), or 4,4'-bis[N,N'-3-tolylamino]-3,3'-dimethylbiphenyl (HMTPD).

8. The heterostructure light-emitting device of claim 6, wherein the hole transporting layer is naphthylphenylbiphenylamine (NPB), or 4,4'-bis[N,N'-3-tolylamino]-3,3'-dimethylbiphenyl (HMTPD).

9. The heterostructure light-emitting device of claim 5, wherein the hole blocking layer is 4-biphenyloxolato 4,4'-N,N'-dicarbazole-biphenyl (CBP), aluminum(III)bis(2-methyl-8-quinolinato)4-phenylphenolate (BAlq), or bathocuproine (BCP).

10. The heterostructure light-emitting device of claim 6, wherein the hole blocking layer is 4-biphenyloxolato 4,4'-N,N'-dicarbazole-biphenyl (CBP), aluminum(III)bis(2-methyl-8-quinolinato)4-phenylphenolate (BAlq), or bathocuproine (BCP).

11. The heterostructure light-emitting device of claim 5, wherein the electron transporting layer is tris(8-quinolinolato)aluminum (Alq3).

12. The heterostructure light-emitting device of claim 6, wherein the electron transporting layer is tris(8-quinolinolato)aluminum (Alq3).

13. The heterostructure light-emitting device of claim 5, wherein the host material is naphthylphenylbiphenylamine (NPB), 3-phenyl-4-(1'-naphthyl)-5-phenyl-1,2,4-triazole (TAZ), bathocuproine (BCP), 4,4'-N,N'-dicarbazole-biphenyl (CBP), or 1,3-bis(N,N'-t-butylphenyl)-1,3,4-oxadiazole (OXD7).

14. The heterostructure light-emitting device of claim 6, wherein the host material is naphthylphenylbiphenylamine (NPB), 3-phenyl-4-(1'-naphthyl)-5-phenyl-1,2,4-triazole (TAZ), bathocuproine (BCP), 4,4'-N,N'-dicarbazole-biphenyl (CBP), or 1,3-bis(N,N'-t-butylphenyl)-1,3,4-oxadiazole (OXD7).

15. The heterostructure light-emitting device of claim 6, wherein the blue emissive layer comprises 9,10-bis-(β-naphthyl)-anthracene (BNA), naphthylphenylbiphenylamine (NPB), 3-phenyl-4-(1'-naphthyl)-5-phenyl-1,2,4-triazole (TAZ), 4-biphenyloxolato 4,4'-N,N'-dicarbazole-biphenyl (CBP), bathocuproine (BCP), aluminum(III) bis(2-methyl-8-quinolinato)4-phenylphenolate (BAlq), or 1,3-bis(N,N'-t-butylphenyl)-1,3,4-oxadiazole (OXD7).

16. The heterostructure light-emitting device of claim 5, further comprising a plurality of emissive layers.

17. The heterostructure light-emitting device of claim 6, further comprising a plurality of emissive layers.

18. The heterostructure light-emitting device of claim 5, further comprising at least one filter layer.

19. The heterostructure light-emitting device of claim 6, further comprising at least one filter layer.

20. The heterostructure light-emitting device of claim 6, wherein the device emits orange light at CIE_1931 coordinates of (0.37, 0.58).

21. The heterostructure light-emitting device of claim 6, wherein the device emits white light at CIE_1931 coordinates from about (0.26, 0.31) to about (0.33, 0.39), with increasing voltage.

22. The heterostructure light-emitting device of claim 6, wherein the device emits white-light with distinct emission peak maxima at 436, 532 and 570 nm in an electroluminescent spectrum.

23. A flat panel display comprising at least one heterostructure light-emitting device of claim 5.

24. A flat panel display comprising at least one heterostructure light-emitting device of claim 6.

25. A method of fabricating a light-emitting device, the method comprising:
depositing a first electrode on a substrate;
depositing a hole transporting layer on the first electrode;
depositing at least one emissive layer on the hole transport layer, the emissive layer comprising at least one host material and/or one emitting/dopant complex, wherein the emitting/dopant complex is the organometallic complex of claim 1;
depositing a hole blocking layer on the emissive layer;
depositing an electron transporting layer on the hole blocking layer; and
depositing a second electrode on the electron transporting layer.

26. A method of fabricating a light-emitting device, the method comprising:
depositing a first electrode on a substrate;
depositing a hole transporting layer on the first electrode;
depositing at least one emissive layer on the hole transport layer, the emissive layer comprising at least one host material and/or one emitting/dopant complex, wherein the emitting/dopant complex is the organometallic complex of claim 1;
depositing a hole transporting layer on the emissive layer;
depositing a blue emissive layer on the hole transporting layer;
depositing a hole blocking layer on the blue emissive layer;
depositing an electron transporting layer on the hole blocking layer; and
depositing a second electrode on the electron transporting layer.

* * * * *